United States Patent
Kawasaki et al.

(10) Patent No.: US 6,946,472 B2
(45) Date of Patent: Sep. 20, 2005

(54) POLYCYCLIC COMPOUNDS EXHIBITING ANTI-TUMOR ACTIVITIES

(75) Inventors: Kenichi Kawasaki, Fujisawa (JP); Tatsuo Ohtsuka, Kamakura (JP); Kiyoaki Sakata, Sagamihara (JP)

(73) Assignee: Hoffman-La Roche Inc., Nutley, NJ (US)

( * ) Notice: Subject to any disclaimer, the term of this patent is extended or adjusted under 35 U.S.C. 154(b) by 250 days.

(21) Appl. No.: 10/414,640

(22) Filed: Apr. 16, 2003

(65) Prior Publication Data

US 2003/0229098 A1 Dec. 11, 2003

(30) Foreign Application Priority Data

Apr. 30, 2002 (EP) .............................. 02009303

(51) Int. Cl.[7] .................. A61K 31/473; A61K 31/435; A61K 31/44; A61K 31/495; C07D 471/02
(52) U.S. Cl. .................. 514/285; 546/70; 546/65; 546/58; 544/233; 514/280; 514/257; 514/250; 514/248
(58) Field of Search ................ 514/285, 280, 514/257, 250, 248; 546/70, 65, 58; 544/233, 246, 343

(56) References Cited

U.S. PATENT DOCUMENTS 6,680,326 B2 * 1/2004 Aoyama et al. ............. 514/285

FOREIGN PATENT DOCUMENTS

EP         713 870 A1      5/1996
WO         WO 98 45272     10/1998
WO         WO 99 64054     12/1999
WO         WO 03 031444    4/2003

OTHER PUBLICATIONS

Binder, D., Monatshefte für Chemie, 105, pp. 179–186 (1974).
Allan et al., Aust. J. Chem., 36, pp. 1221–1226 (1983).

* cited by examiner

*Primary Examiner*—James O. Wilson
*Assistant Examiner*—Matthew L. Fedowitz
(74) *Attorney, Agent, or Firm*—George W. Johnston; Patricia S. Rocha-Tramaloni

(57) ABSTRACT

This invention is concerned with novel polycyclic compounds of formula [I],

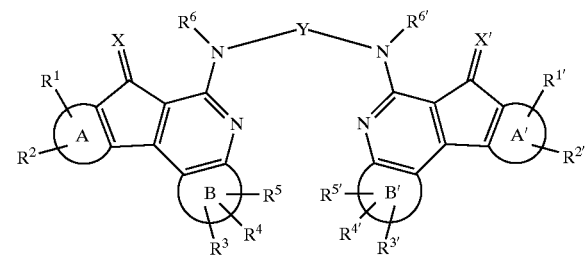

wherein ring A, ring B, $R^1$, $R^2$, $R^3$, $R^4$, $R^5$, $R^6$, X, Y, $R^{1'}$, $R^{2'}$, $R^{3'}$, $R^{4'}$, $R^{5'}$, $R^{6'}$, ring A', ring B' and X' are as defined hereinabove as well as pharmaceutically acceptable salts thereof. The compounds have anti-tumor activity and are useful for the treatment of cell proliferative disorders.

28 Claims, No Drawings

POLYCYCLIC COMPOUNDS EXHIBITING ANTI-TUMOR ACTIVITIES

FIELD OF THE INVENTION

The present invention relates to novel polycyclic compounds having anti-tumor activity, pharmaceutical composition containing these compounds, the use of those compounds in the medical therapy as well as the process for the preparation of those compounds.

BACKGROUND OF THE INVENTION

Indeno[2,1-c]quinolin-7-one derivatives having a substituted aminoalkylamino group as a side chain are known to have anti-tumor activity. For example 6-(2-dimethylaminoethylamino)-3-hydroxy-7H-indeno[2,1-c]quinolin-7-one and its derivatives have been disclosed by Taiho Pharmaceutical Co. Ltd. [EP 0713870 (1996)] to have anti-tumor activity. However, its activity may not be sufficient for the treatment of solid tumors and thus, more potent anti-tumor compounds are desirable. It is therefore desirable to provide more potent compounds for treatment of tumors.

SUMMARY OF THE INVENTION

In particular, the present invention relates to novel polycyclic compounds of formula [I],

[I]

wherein
ring A is an unsubstituted nitrogen-containing 5 or 6 membered heteroaromatic ring or a substituted nitrogen-containing 5 or 6 membered heteroaromatic ring substituted by one or two groups independently selected from $R^1$ and $R^2$;

ring A' is an unsubstituted nitrogen-containing 5 or 6 membered heteroaromatic ring or a substituted nitrogen-containing 5 or 6 membered heteroaromatic ring substituted by one or two groups independently selected from $R^{1'}$ and $R^{2'}$;

ring B is an unsubstituted benzene ring, or a substituted benzene ring substituted by 1 to 3 groups independently selected from $R^3$, $R^4$ and $R^5$, an unsubstituted naphthalene ring, or a substituted naphthalene ring substituted by 1 to 3 groups independently selected from $R^3$, $R^4$ and $R^5$, a benzene ring substituted with a $(C_1-C_5)$ alkylenedioxy group, or a substituted benzene ring substituted with a $(C_1-C_5)$ alkylenedioxy group further substituted by 1 to 3 groups independently selected from $R^3$, $R^4$ and $R^5$;

ring B' is an unsubstituted benzene ring, or a substituted benzene ring substituted by 1 to 3 groups independently selected from $R^3$, $R^4$ and $R^5$, an unsubstituted naphthalene ring, or a substituted naphthalene ring substituted by 1 to 3 groups independently selected from $R^3$, $R^4$ and $R^5$, a benzene ring substituted with a $(C_1-C_5)$-alkylenedioxy group, or a substituted benzene ring substituted with a $(C_1-C_5)$-alkylenedioxy group further substituted by 1 to 3 groups independently selected from $R^3$, $R^4$ and $R^5$;

$R^1$, $R^2$, $R^{1'}$ and $R^{2'}$ are independently selected from the group consisting of hydrogen, halogen, hydroxy, mercapto, $(C_1-C_5)$-alkyl, $(C_1-C_5)$-halogenalkyl, $(C_1-C_5)$-alkoxy, $(C_1-C_5)$ halogenalkoxy, $(C_3-C_5)$-alkenyloxy, $(C_4-C_7)$-cycloalkyloxy, $(C_3-C_7)$-cyloalkyl $(C_1-C_5)$ alkyloxy, aryl $(C_1-C_5)$ alkyloxy, $(C_1-C_5)$ alkylthio, $(C_1-C_5)$-alkylsulfinyl, $(C_1-C_5)$-alkylsulfonyl, amino, mono-$(C_1-C_5)$-alkylamino and di-$(C_1-C_5)$-alkylamino;

$R^3$, $R^4$, $R^5$, $R^{3'}$, $R^{4'}$ and $R^{5'}$ are independently selected from the group consisting of hydrogen, halogen, hydroxy, mercapto, $(C_1-C_5)$-alkyl, $(C_3-C_7)$-cycloalkyl, $(C_1-C_5)$-halogenalkyl, $(C_1-C_5)$-alkoxy, $(C_1-C_5)$ halogenalkoxy, $(C_3-C_5)$-alkenyloxy, $(C_4-C_7)$-cycloalkyloxy, $(C_3-C_7)$-cyloalkyl $(C_1-C_5)$ alkyloxy, aryl $(C_1-C_5)$ alkyloxy, $(C_1-C_5)$ alkylthio, $(C_1-C_5)$-alkylsulfinyl, $(C_1-C_5)$-alkylsulfonyl, amino, mono-$(C_1-C_5)$-alkylamino and di-$(C_1-C_5)$-alkylamino;

X is =O or =N—O—$R^7$, wherein $R^7$ is a hydrogen, $(C_1-C_5)$-alkyl, $(C_3-C_5)$-alkenyl, $(C_4-C_7)$-cycloalkyl, $(C_3-C_7)$-cycloalkyl$(C_1-C_5)$-alkyl, aryl, or aryl$(C_1-C_5)$-alkyl;

X' is =O or =N—O—$R^7$, wherein $R^7$ is a hydrogen, $(C_1-C_5)$-alkyl, $(C_3-C_5)$-alkenyl, $(C_4-C_7)$-cycloalkyl, $(C_3-C_7)$-cycloalkyl$(C_1-C_5)$-alkyl, aryl, or aryl$(C_1-C_5)$-alkyl;

$R^6$ is hydrogen, unsubstituted $(C_1-C_5)$-alkyl or substituted $(C_1-C_5)$-alkyl substituted by 1 to 3 groups independently selected from hydroxy, amino or halogen;

$R^{6'}$ is hydrogen, unsubstituted $(C_1-C_5)$-alkyl or substituted $(C_1-C_5)$ alkyl substituted by 1 to 3 groups independently selected from hydroxy, amino or halogen;

Y is -[J-N($R^8$)]p-[K-N($R^9$)]q-L- or -J-M-L-, wherein J, K and L are the same or different unsubstituted $(C_2-C_5)$-alkylenes or substituted $(C_2-C_5)$-alkylenes substituted with 1 or 2 $(C_1-C_5)$-alkyl; M is an aliphatic ring having 2 nitrogen atoms; p and q are the same or different integers of 0 to 2; and $R^8$ and $R^9$ are independently hydrogen or $(C_1-C_5)$-alkyl, or a pharmaceutically acceptable salt thereof.

It is another aspect of the present invention to provide pharmaceutical compositions containing these compounds, and the use of those compounds in the medical therapy, especially in treatment of tumor.

A still further aspect of the present invention is to provide a process for the preparation of those compounds.

DETAILED DESCRIPTION OF THE INVENTION

Unless otherwise indicated, the following definitions are set forth to illustrate and define the meaning and scope of the various terms used to describe the present invention herein.

In this specification the term "nitrogen-containing 5 or 6 membered heteroaromatic ring" is used to mean a group of a 5 to 6 membered aromatic ring which contains at least one nitrogen atom and may further contain one or more heteroatom(s) selected from N, S and O. Preferably, "nitrogen-containing 5 or 6 membered heteroaromatic ring" means pyridine, pyrazine, pyridazine, pyrimidine, oxazole, thiazole, isoxazole, isothiazole, imidazole, pyrrole, triazole and the like. More preferably, this term refers to pyridine.

The term "alkyl" as used herein, alone or in combination, means a straight-chain or branched-chain hydrocarbon group containing a maximum of 12, preferably a maximum of 5, carbon atoms, e.g., methyl, ethyl, n-propyl, 2-methylpropyl (iso-butyl), 1-methylethyl (iso-propyl), n-butyl, and 1,1-dimethylethyl (t-butyl), and more preferably a maximum of 4 carbon atoms. The alkyl group may be unsubstituted or may be substituted with one or more substituents, preferably with 1 to 3 substituents, most preferably with one substituent. The substituents are selected from the group consisting of hydroxy, alkoxy, amino, mono- or di-alkylamino, acetoxy, alkylcarbonyloxy, alkoxycarbonyl, carbamoyl and/or halogen.

The term "alkenyl" as used therein, alone or in combination, refers to a hydrocarbon chain as defined for alkyl having at least one olefinic double bond (including for example, allyl and butenyl) and having the general formula $C_mH_{2m-1}$, wherein m is an integer greater than 2, preferably m is an integer between 3 to 7, more preferably between 3 to 5.

The term "alkylene" refers to a branched or unbranched hydrocarbon chain containing 1 to 5 carbon atoms, such as methylene (—$CH_2$—), ethylene, propylene, trimethylene and tetramethylene. The alkylene group may be unsubstituted or may be substituted with one or more substituents, preferably with 1 to 3 substituents, most preferably with one substituent. The substituents are selected from the group consisting of hydroxy, alkoxy, amino, mono- or di-alkylamino, acetoxy, alkylcarbonyloxy, alkoxycarbonyl, carbamoyl and/or halogen.

The term "aryl" refers to an aromatic carbocyclic group, i.e. a 6 or 10 membered aromatic or partially aromatic ring, e.g. phenyl (i.e. "Ph"), naphthyl or tetrahydro-naphthyl, preferably phenyl or naphthyl, and most preferably phenyl. The aryl moiety may be substituted with one or more substituents, preferably with 1 to 3, most preferably one, selected from the group consisting of halogen (preferably fluorine or chlorine), alkoxycarbonyl (e.g. methoxycarbonyl), alkylcarbonyloxy (e.g., acetoxy), cyano, alkyl, alkoxy, phenyl, phenoxy, trifluoromethyl, trifluoromethoxy, alkylthio, hydroxy, alkylcarbonylamino, heterocyclyl, sulfamoyl (i.e. $H_2NSO_2$—), amino, 1,3-dioxolyl and/or 1,4-dioxolyl. Especially preferred substituents are alkyl, alkoxy, hydroxy, halogen, amino, alkylamino, dialkylamino, alkylthio, sulfamoyl, benzyl or heterocyclyl.

The term "aryl($C_1$–$C_5$)-alkyl" refers to an alkyl group as defined above substituted with an aryl as defined above. The aryl group of the aryl($C_1$–$C_5$)-alkyl may be substituted with one or more substituents, preferably 1 to 3, most preferably with one substituent selected from the group consisting of halogen (preferably fluorine or chlorine), alkoxycarbonyl, (e.g. methoxycarbonyl), alkylcarbonyloxy (e.g., acetoxy), cyano, alkyl, alkoxy, phenyl, phenoxy, trifluoromethyl, trifluoromethoxy, alkylthio, hydroxy, alkylcarbonylamino, heterocyclyl, sulfamoyl, amino, 1,3-dioxolyl and/or 1,4-dioxolyl.

Especially preferred substituents of aryl($C_1$–$C_5$)-alkyl are alkoxy, hydroxy, halogen, amino, mono- or di-alkylamino or alkylthio.

The term "alkoxy" refers to the group —O—R' wherein R' is an alkyl as defined above.

"Aryl($C_1$–$C_5$)-alkyloxy" refers to the group —O—R* wherein R* is aryl($C_1$–$C_5$)-alkyl as defined above.

The term "cycloalkyl" signifies a saturated, cyclic hydrocarbon group with 3–7 carbon atoms, preferably with 4–7 carbon atoms, more preferably 4–6 carbon atoms, i.e. cyclopropyl, cyclobutyl, cyclopentyl and cyclohexyl and the like. The cycloalkyl group may be substituted or unsubstituted. The substituents are selected from alkyl, phenyl, amino, hydroxy and/or halogen.

The term "($C_3$–$C_7$)-cycloalkyl($C_1$–$C_5$)-alkyl" refers to a branched or straight chain monovalent saturated aliphatic carbon group of 1 to 5, preferably 1 to 3 carbon atom(s) having a monovalent carbocyclic group of 3 to 7 carbon atoms, preferably 3 to 6 carbon atoms.

The term "aliphatic ring" refers to a carbocyclic group of 3 to 7 carbon atoms, preferably 3 to 6 carbon atoms, such as cyclopropane, cyclobutane, cyclopentane and cyclohexane, which may contain 1 to 3 heteroatom(s), preferably 1 to 2, selected from oxygen, nitrogen and sulfur. The examples of aliphatic ring containing heteroatom(s) are morpholine ring, thiomorpholine ring, pyrrolidine ring, piperidine ring and piperazine ring.

The term "alkylthio" refers to the group —S—R", wherein R" is an alkyl group as defined above.

The term "amino" refers to the group —$NH_2$ and includes amino groups which are protected by a group known in the art such as a benzyloxycarbonyl group, acetyl group, alkoxycarbonyl group or benzyl group and the like.

The term "halogen" refers to fluoro, chloro, bromo and iodo.

The term "heteroatom" refers to oxygen, nitrogen and sulfur.

The term "hydroxy" refers to the group —OH.

The term "cyano" refers to the group —CN.

The term "mercapto" refers to the group —SH.

The term "($C_3$–$C_7$)-cycloalkyl($C_1$–$C_5$)-alkyloxy" means the group —O—$R^{3'}$ wherein $R^{3'}$ is a cycloalkyl-alkyl group as defined above.

The term "($C_1$–$C_5$)-alkylsulfinyl" means the group —SO—$R^{4'}$ wherein $R^{4'}$ is an ($C_1$–$C_5$)-alkyl group as defined above.

The term "($C_1$–$C_5$)-alkylsulfonyl" means the group —$SO_2$—$R^{5'}$ wherein $R^{5'}$ is an ($C_1$–$C_5$)-alkyl group as defined above.

The term "halogen($C_1$–$C_5$)-alkyl" means alkyl substituted with one or more halogen atoms.

"Halogen($C_1$–$C_5$)-alkyloxy" refers to the group —O-halogen($C_1$–$C_5$)-alkyl.

The term "alkenyloxy" means the group —O—$R^{6'}$ wherein $R^{6'}$ is an alkenyl group as defined above.

The term "cycloalkyloxy" means the group —O—$R^{7'}$ wherein $R^{7'}$ is a cycloalkyl group as defined above.

The term "mono- and di-alkylamino" refers to an amino group substituted with an alkyl group or two alkyl groups as defined above, i.e., alkyl-NH— and dialkyl-N—.

The term "benzene ring substituted with an ($C_1$–$C_5$)-alkylenedioxy group" preferably means benzo[1,3]dioxole and 2,3-dihydrobenzo[1,4]dioxine, and most preferably benzo[1,3]dioxole.

In the present invention, the expression "optionally substituted" means that substitution may occur at one or more positions, preferably at one to three positions, and, unless otherwise indicated, that the substituents are independently selected from the specified options.

"Pharmaceutically acceptable salt" refers to conventional acid-addition salts or base-addition salts which retain the biological effectiveness and properties of the compounds of formula [I] and are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Sample base-addition salts include those derived from potassium, sodium, ammonium, and quaternary ammonium hydroxide, such as for example tetramethylammonium hydroxide. The term "pharmaceutically acceptable salt" also comprises prodrugs of polycyclic compounds of the formula [I] or corresponding salts thereof.

"Pharmaceutically acceptable", such as pharmaceutically acceptable carrier, excipient, prodrug, etc., means pharmacologically acceptable and substantially non-toxic to the subject to which the particular compound is administered.

"Pharmaceutically active metabolite" means a metabolic product of a compound of the formula [I] which is pharmaceutically acceptable and effective.

The term "prodrug" refers to the compounds of the formula [I] that maybe converted under physiological conditions or by solvolysis to any of the compounds of the formula [I] or to a pharmaceutically acceptable salt of the compounds of the formula [I].

A prodrug may be inactive when administered to a subject but is converted in vivo to an active compound of the formula [I].

In a preferred embodiment, the present invention comprises compounds of the formula [I],

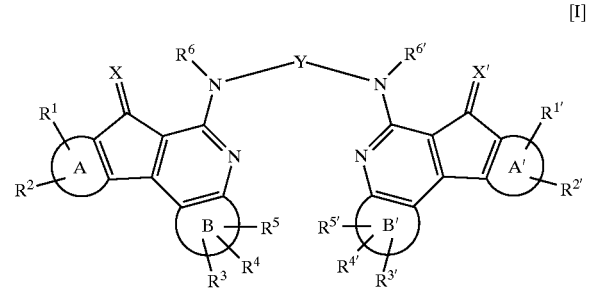

ring A is an unsubstituted nitrogen-containing 5 or 6 membered heteroaromatic ring or a substituted nitrogen-containing 5 or 6 membered heteroaromatic ring substituted by one or two groups independently selected from $R^1$ and $R^2$;

ring A' is an unsubstituted nitrogen-containing 5 or 6 membered heteroaromatic ring or a substituted nitrogen-containing 5 or 6 membered heteroaromatic ring substituted by one or two groups independently selected from $R^{1'}$ and $R^{2'}$;

ring B is an unsubstituted benzene ring, or a substituted benzene ring substituted by 1 to 3 groups independently selected from $R^3$, $R^4$ and $R^5$, an unsubstituted naphthalene ring, or a substituted naphthalene ring substituted by 1 to 3 groups independently selected from $R^3$, $R^4$ and $R^5$, a benzene ring substituted with a $(C_1-C_5)$ alkylenedioxy group, or a substituted benzene ring substituted with a $(C_1-C_5)$ alkylenedioxy group further substituted by 1 to 3 groups independently selected from $R^3$, $R^4$ and $R^5$;

ring B' is an unsubstituted benzene ring, or a substituted benzene ring substituted by 1 to 3 groups independently selected from $R^3$, $R^4$ and $R^5$, an unsubstituted naphthalene ring, or a substituted naphthalene ring substituted by 1 to 3 groups independently selected from $R^3$, $R^4$ and $R^5$, a benzene ring substituted with a $(C_1-C_5)$-alkylenedioxy group, or a substituted benzene ring substituted with a $(C_1-C_5)$-alkylenedioxy group further substituted by 1 to 3 groups independently selected from $R^3$, $R^4$ and $R^5$;

$R^1$, $R^2$, $R^{1'}$ and $R^{2''}$ are independently selected from the group consisting of hydrogen, halogen, hydroxy, mercapto, $(C_1-C_5)$-alkyl, $(C_1-C_5)$-halogenalkyl, $(C_1-C_5)$-alkoxy, $(C_1-C_5)$ halogenalkoxy, $(C_3-C_5)$-alkenyloxy, $(C_4-C_7)$-cycloalkyloxy, $(C_3-C_7)$-cycloalkyl $(C_1-C_5)$ alkyloxy, aryl $(C_1-C_5)$ alkyloxy, $(C_1-C_5)$ alkylthio, $(C_1-C_5)$-alkylsulfinyl, $(C_1-C_5)$-alkylsulfonyl, amino, mono-$(C_1-C_5)$-alkylamino and di-$(C_1-C_5)$-alkylamino;

$R^3$, $R^4$, $R^5$, $R^{3'}$, $R^{4'}$ and $R^{5'}$ are independently selected from the group consisting of hydrogen, halogen, hydroxy, mercapto, $(C_1-C_5)$-alkyl, $(C_3-C_7)$-cycloalkyl, $(C_1-C_5)$-halogenalkyl, $(C_1-C_5)$-alkoxy, $(C_1-C_5)$ halogenalkoxy, $(C_3-C_5)$-alkenyloxy, $(C_4-C_7)$-cycloalkyloxy, $(C_3-C_7)$-cyloalkyl $(C_1-C_5)$ alkyloxy, aryl $(C_1-C_5)$ alkyloxy, $(C_1-C_5)$ alkylthio, $(C_1-C_5)$-alkylsulfinyl, $(C_1-C_5)$-alkylsulfonyl, amino, mono-$(C_1-C_5)$-alkylamino and di-$(C_1-C_5)$-alkylamino;

X is =O or =N—O—$R^7$, wherein $R^7$ is a hydrogen, $(C_1-C_5)$-alkyl, $(C_3-C_5)$-alkenyl, $(C_4-C_7)$-cycloalkyl, $(C_3-C_7)$-cycloalkyl$(C_1-C_5)$-alkyl, aryl, or aryl$(C_1-C_5)$-alkyl;

X' is =O or =N—O—$R^7$, wherein $R^7$ is a hydrogen, $(C_1-C_5)$-alkyl, $(C_3-C_5)$-alkenyl, $(C_4-C_7)$-cycloalkyl, $(C_3-C_7)$-cycloalkyl$(C_1-C_5)$-alkyl, aryl, or aryl$(C_1-C_5)$-alkyl;

$R^6$ is hydrogen, unsubstituted $(C_1-C_5)$-alkyl or substituted $(C_1-C_5)$-alkyl substituted by 1 to 3 groups independently selected from hydroxy, amino or halogen;

$R^{6'}$ is hydrogen, unsubstituted $(C_1-C_5)$-alkyl or substituted $(C_1-C_5)$ alkyl substituted by 1 to 3 groups independently selected from hydroxy, amino or halogen;

Y is -[J-N($R^8$)]p-[K-N($R^9$)]q-L- or -J-M-L-, wherein J, K and L are the same or different unsubstituted $(C_2-C_5)$-alkylenes or substituted $(C_2-C_5)$-alkylenes substituted with 1 or 2 $(C_1-C_5)$-alkyl; M is an aliphatic ring having 2 nitrogen atoms; p and q are the same or different integers of 0 to 2; and $R^8$ and $R^9$ are independently hydrogen or $(C_1-C_5)$-alkyl, or a pharmaceutically acceptable salt thereof.

In a preferred embodiment, the invention comprises compounds of the formula [I] wherein ring A is a nitrogen-containing 5 or 6 membered heteroaromatic ring that may be substituted by $R^1$ and $R^2$. Preferably, ring A is a pyridine, pyrazine, pyridazine or pyrimidine ring, and more preferably a pyridine ring.

In a preferred embodiment, the invention comprises compounds of the formula [I] wherein ring A' is a nitrogen-containing 5 or 6 membered heteroaromatic ring that may be substituted by $R^{1'}$ and $R^{2'}$. Preferably, ring A' is a pyridine, pyrazine, pyridazine or pyrimidine ring, and more preferably a pyridine ring.

In more detail, the present invention refers to compounds as described above wherein ring A and ring A' are independently selected from the group consisting of pyridine, pyrazine, pyridazine, pyrimidine, oxazole, thiazole, isoxazole, isothiazole, imidazole, pyrrole, and triazole, optionally substituted with $R^1$ and $R^2$ and $R^{1'}$ and $R^{2'}$, respectively, more preferably the nitrogen-containing 5 or 6 membered heteroaromatic ring A and A' are pyridine, that may be substituted with $R^1$ and $R^2$, and $R^{1'}$ and $R^{2'}$, respectively.

In a preferred embodiment, ring B is a benzene ring that may be substituted by 1 to 3 groups independently selected from $R^3$, $R^4$ and $R^5$, a naphthalene ring that may be substituted by 1 to 3 groups independently selected from $R^3$, $R^4$ and $R^5$, or a benzene ring substituted with a $(C_1-C_5)$- alkylenedioxy group which ring may be substituted by 1 to 3 groups independently selected from $R^3$, $R^4$ and $R^5$. In a further preferred embodiment, the invention comprises compounds of the formula [I], wherein ring B is a benzene ring or a benzo[1,3] dioxole that may be substituted by 1 to 3 groups independently selected from $R^3$, $R^4$ and $R^5$. Most preferably, ring B is a benzene ring that may be substituted by 1 to 3 groups independently selected from $R^3$, $R^4$ and $R^5$.

In a preferred embodiment, ring B' is a benzene ring that may be substituted by 1 to 3 groups independently selected from $R^{3'}$, $R^{4'}$ and $R^{5'}$, a naphthalene ring that may be substituted by 1 to 3 groups independently selected from $R^{3'}$, $R^{4'}$ and $R^{5'}$, or a benzene ring substituted with a $(C_1-C_5)$-alkylenedioxy group which ring that may be substituted by 1 to 3 groups independently selected from $R^{3'}$, $R^{4'}$ and $R^{5'}$. In a further preferred embodiment, the invention comprises compounds of the formula [I], wherein ring B' is a benzene ring or benzo[1,3] dioxole that may be substituted by 1 to 3 groups independently selected from $R^{3'}$, $R^{4'}$ and $R^{5'}$. Most preferably, ring B' is a benzene ring that may be substituted by 1 to 3 groups independently selected from $R^{3'}$, $R^{4'}$ and $R^{5'}$.

In more detail, the present invention refers to compounds as described above wherein ring B and ring B' are independently selected from a benzene ring, naphthalene ring or benzene ring having $(C_1-C_5)$ alkylenedioxy group which rings may be substituted by $R^3$, $R^4$ and $R^5$, or $R^{3'}$, $R^{4'}$ and $R^{5'}$ respectively, more preferably to compounds as described above wherein ring B and ring B' are independently selected from a benzene or benzo[1,3] dioxole ring which rings may be substituted by $R^3$, $R^4$ and $R^5$ or $R^{3'}$, $R^{4'}$ and $R^{5'}$ respectively, and most preferably wherein ring B and ring B' are benzene rings which independently may be substituted by $R^3$, $R^4$ and $R^5$ or $R^{3'}$, $R^{4'}$ and $R^{5'}$ respectively.

In a preferred embodiment, the invention comprises compounds of the formula [I], wherein one of $R^1$ and $R^2$ is hydrogen, halogen or $(C_1-C_5)$-alkyl. More preferably, one of $R^1$ and $R^2$ is hydrogen and the other one is —$CH_3$.

In another preferred embodiment, the present invention comprises compounds of the formula [I], wherein $R^1$ is hydrogen and $R^2$ is —$CH_3$.

In another preferred embodiment, the present invention comprises compounds of the formula [I], wherein $R^1$ and $R^2$ are hydrogen.

In a preferred embodiment, the invention comprises compounds of the formula [I], wherein one of $R^{1'}$ and $R^{2'}$ is hydrogen, halogen or $(C_1-C_5)$-alkyl. More preferably, one of $R^{1'}$ and $R^{2'}$ is hydrogen and the other one is —$CH_3$.

In another preferred embodiment, the present invention comprises compounds of the formula [I], wherein $R^{1'}$ is hydrogen and $R^{2'}$ is —$CH_3$.

In another preferred embodiment, the present invention comprises compounds of the formula [I], wherein $R^{1'}$ and $R^{2'}$ are hydrogen.

In a further preferred embodiment, the present invention comprises compounds of the formula [I], wherein $R^1$, $R^2$, $R^{1'}$ and $R^{2'}$ are all hydrogen.

In a preferred embodiment, the invention comprises compounds of the formula [I], wherein X and X' are =O or =N—$OCH_3$. More preferably, X and X' are =O.

In a preferred embodiment, the invention comprises compounds of the formula [I], wherein $NR^6$ is —NH—.

In a further preferred embodiment, the invention comprises compounds of the formula [I], wherein $NR^{6'}$ is —NH—.

In a preferred embodiment, the present invention comprises compounds of the formula [I] wherein $R^3$, $R^4$ and $R^5$ are hydrogen; or wherein one of $R^3$, $R^4$ and $R^5$ is halogen and the two others are hydrogen; or wherein one of $R^3$, $R^4$ and $R^5$ one is —$OCH_3$ and the two others are hydrogen; or wherein one of $R^3$, $R^4$ and $R^5$ is —OH and the two others are hydrogen.

Most preferably, the present invention comprises polycyclic compounds of the formula [I] wherein one of $R^3$, $R^4$ and $R^5$ is chloro and the two others are hydrogen. Also preferred are compounds of formula [I] wherein $R^3$ is —$OCH_3$, and $R^4$ and $R^5$ are hydrogen.

In a preferred embodiment, the present invention comprises compounds of the formula [I] wherein $R^{3'}$, $R^{4'}$ and $R^{5'}$ are hydrogen; or one of $R^{3'}$, $R^{4'}$ and $R^{5'}$ is halogen and the two others are hydrogen; or one of $R^{3'}$, $R^{4'}$ and $R^{5'}$ is —$OCH_3$ and the two others are hydrogen; or one of $R^{3'}$, $R^{4'}$ and $R^{5'}$ is —OH and the two others are hydrogen.

Most preferably, the present invention comprises polycyclic compounds of formula [I] wherein one of $R^{3'}$, $R^{4'}$ and $R^{5'}$ is chloro and the two others are hydrogen. Also preferred are compounds of formula [I] wherein $R^{3'}$ is —$OCH_3$, and $R^{4'}$ and $R^{5'}$ are hydrogen.

In another preferred embodiment of the present invention, $R^3$, $R^4$, $R^5$, $R^{3'}$, $R^{4'}$ and $R^{5'}$ are all hydrogen in the polycyclic compounds of formula [I].

In a further preferred embodiment, the present invention comprises polycyclic compounds of formula [I] wherein $R^3$ and $R^{3'}$ are both chloro; and $R^4$, $R^5$, $R^{4'}$ and $R^{5'}$ are all hydrogen.

In another preferred embodiment, the present invention concerns polycyclic compounds of formula [I], wherein $R^3$ is —$OCH_3$; and $R^{3'}$, $R^4$, $R^5$, $R^{4'}$ and $R^{5'}$ are all hydrogen.

Preferably, the present invention comprises polycyclic compounds of formula [I], wherein —$N(R^6)$—Y—$N(R^6)$— is selected from the group consisting of —NH—$CH_2CH_2$—$N(CH_3)$—$CH_2CH_2NH$—,
—NH—$CH_2CH_2CH_2$—$N(CH_3)$—$CH_2CH_2CH_2NH$—,
—NH—$CH_2CH_2$—$N(CH_3)$—$CH_2CH_2$—$N(CH_3)$—$CH_2CH_2NH$—,
—NH—$CH_2CH_2$—$N(CH_3)$—$CH_2CH_2CH_2$—$N(CH_3)$—$CH_2CH_2NH$—, and

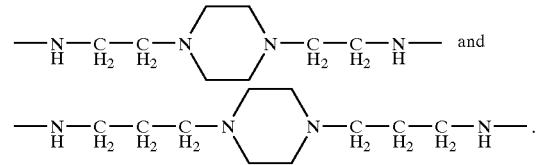

More preferably, the present invention comprises polycyclic compounds of formula [I], wherein —$N(R^6)$—Y—$N(R^6)$— is

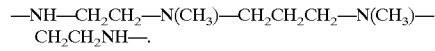

Preferred polycyclic compounds of formula [I] as well as pharmaceutically acceptable salts thereof in accordance with the present invention are as follows:

a) 3-methoxy-6-(2-{methyl-[2-(3-methoxy-7-oxo-7H-5,9-diaza-benzo[c]fluoren-6-ylamino)-ethyl]-amino}-ethylamino)-5,9-diaza-benzo[c]fluoren-7-one, b) 3-methoxy-6-{2-[(2-{[2-(3-methoxy-7-oxo-7H-5,9-diaza-benzo[c]fluoren-6-ylamino)-ethyl]-methyl-amino}-ethyl)-methyl-amino]-ethylamino}-5,9-diaza-benzo[c]fluoren-7-one, c) 3-methoxy-6-{2-[(3-{[2-(3-methoxy-7-oxo-7H-5,9-diaza-benzo[c]fluoren-6-ylamino)-ethyl]-methylamino}-propyl)-methyl-amino]-ethylamino}-5,9-diaza-benzo[c]fluoren-7-one, d) 6-(3-{methyl-[3-(7-oxo-7H-5,9-diaza-benzo[c]fluoren-6-ylamino)-propyl]-amino}-propylamino)-5,9-diaza-benzo[c]fluoren-7-one, e) 6-{2-[methyl-(3-{methyl-[2-(7-oxo-7H-5,9-diaza-benzo[c]fluoren-6-ylamino)-ethyl]-amino}-propyl)-amino]-ethylamino}-5,9-diaza-benzo[c]fluoren-7-one, f) 3-chloro-6-{2-[(3-{[2-(3-chloro-7-oxo-7H-5,9-diaza-benzo[c]fluoren-6-ylamino)-ethyl]-methyl-amino}-propyl)-methyl-amino]-ethylamino}-5,9-diaza-benzo[c]fluoren-7-one, g) 6-(2-{4-[2-(7-oxo-7H-5,9-diaza-benzo[c]fluoren-6-ylamino)-ethyl]-piperazin-1-yl}-ethylamino)-5,9-diaza-benzo[c]fluoren-7-one, h) 6-(3-{4-[3-(7-oxo-7H-5,9-diaza-benzo[c]fluoren-6-ylamino)-propyl]-piperazin-1-yl}-propylamino)-5,9-diaza-benzo[c]fluoren-7-one, i) 3-methoxy-6-{2-[(3-{[2-(3-methoxy-8-methyl-7-oxo-7H-5,9-diaza-benzo[c]fluoren-6-ylamino)-ethyl]-methyl-amino}-propyl)-methyl-amino]-ethylamino}-8-methyl-5,9-diaza-benzo[c]fluoren-7-one, j) 6-{2-[methyl-(3-{methyl-[2-(7-oxo-7H-5,10-diaza-benzo[c]fluoren-6-ylamino)-ethyl]-amino}-propyl)-amino]-ethylamino}-5,10-diaza-benzo[c]fluoren-7-one, k) 3-methoxy-6-{2-[(3-{[2-(3-methoxy-4-methyl-7-oxo-7H-5,10-diaza-benzo[c]fluoren-6-ylamino)-ethyl]-methyl-amino}-propyl)-methyl-amino]-ethylamino}-4-methyl-5,10-diaza-benzo[c]fluoren-7-one, l) 3-chloro-6-{2-[(3-{[2-(3-chloro-7-oxo-7H-5,10-diaza-benzo[c]fluoren-6-ylamino)-ethyl]-methyl-amino}-propyl)-methyl-amino]-ethylamino}-5,10-diaza-benzo[c]fluoren-7-one, m) 11-chloro-6-{2-[(3-{[2-(11-chloro-3-methoxy-4-methyl-7-oxo-7H-5,10-diaza-benzo[c]fluoren-6-ylamino)-ethyl]-methyl-amino}-propyl)-methyl-amino]-ethylamino}-3-methoxy-4-methyl-5,10-diaza-benzo[c]fluoren-7-one, n) 3-methoxy-6-{2-[(3-{[2-(3-methoxy-9-methyl-7-oxo-7H-5,10-diaza-benzo[c]fluoren-6-ylamino)-ethyl]-methyl-amino}-propyl)-methyl-amino]-ethylamino}-9-methyl-5,10-diaza-benzo[c]fluoren-7-one, o) 6-{2-[methyl-(3-{methyl-[2-(7-oxo-7H-5,10-diaza-benzo[c]fluoren-6-ylamino)-ethyl]-amino}-propyl)-amino]-ethylamino}-5,9-diaza-benzo[c]fluoren-7-one, p) 3-methoxy-6-{2-[methyl-(3-{methyl-[2-(7-oxo-7H-5,9-diaza-benzo[c]fluoren-6-ylamino)-ethyl]-amino}-propyl)-amino]-ethylamino}-5,9-diaza-benzo[c]fluoren-7-one, q) 3-hydroxy-6-{2-[(3-{[2-(3-hydroxy-7-oxo-7H-5,9-diaza-benzo[c]fluoren-6-ylamino)-ethyl]-methyl-amino}-propyl)-methyl-amino]-ethylamino}-5,9-diaza-benzo[c]fluoren-7-one, and r) 6-(3-{[3-(7-methoxyimino-7H-5,9-diaza-benzo[c]fluoren-6-ylamino)-propyl]-methyl-amino}-propylamino)-5,9-diaza-benzo[c]fluoren-7-one O-methyl-oxime.

Especially preferred polycyclic compounds of formula [I] in accordance with the present invention are as follows:

(i) 3-methoxy-6-{2-[(3-{[2-(3-methoxy-7-oxo-7H-5,9-diaza-benzo[c]fluoren-6-ylamino)-ethyl]-methyl-amino}-propyl)-methyl-amino]-ethylamino}-5,9-diaza-benzo[c]fluoren-7-one, (ii) 6-{2-[methyl-(3-{methyl-[2-(7-oxo-7H-5,9-diaza-benzo[c]fluoren-6-ylamino)-ethyl]-amino}-propyl)-amino]-ethylamino}-5,9-diaza-benzo[c]fluoren-7-one, (iii) 3-chloro-6-{2-[(3-{[2-(3-chloro-7-oxo-7H-5,9-diaza-benzo[c]fluoren-6-ylamino)-ethyl]-methyl-amino}-propyl)-methyl-amino]-ethylamino}-5,9-diaza-benzo[c]fluoren-7-one, (iv) 6-(3-{4-[3-(7-oxo-7H-5,9-diaza-benzo[c]fluoren-6-ylamino)-propyl]-piperazin-1-yl}-propylamino)-5,9-diaza-benzo[c]fluoren-7-one, (v) 6-{2-[methyl-(3-{methyl-[2-(7-oxo-7H-5,10-diaza-benzo[c]fluoren-6-ylamino)-ethyl]-amino}-propyl)-amino]-ethylamino}-5,10-diaza-benzo[c]fluoren-7-one, (vi) 3-chloro-6-{2-[(3-{[2-(3-chloro-7-oxo-7H-5,10-diaza-benzo[c]fluoren-6-ylamino)-ethyl]-methyl-amino}-propyl)-methyl-amino]-ethylamino}-5,10-diaza-benzo[c]fluoren-7-one, (vii) 3-methoxy-6-{2-[(3-{[2-(3-methoxy-9-methyl-7-oxo-7H-5,10-diaza-benzo[c]fluoren-6-ylamino)-ethyl]-methyl-amino}-propyl)-methyl-amino]-ethylamino}-9-methyl-5,10-diaza-benzo[c]fluoren-7-one, (viii) 6-{2-[methyl-(3-{methyl-[2-(7-oxo-7H-5,10-diaza-benzo[c]fluoren-6-ylamino)-ethyl]-amino}-propyl)-amino]-ethylamino}-5,9-diaza-benzo[c]fluoren-7-one, and (ix) 3-methoxy-6-{2-[methyl-(3-{methyl-[2-(7-oxo-7H-5,9-diaza-benzo[c]fluoren-6-ylamino)-ethyl]-amino}-propyl)-amino]-ethylamino}-5,9-diaza-benzo[c]fluoren-7-one.

The present invention concerns also a pharmaceutical composition comprising a polycyclic compound of formula [I] as an active ingredient and a pharmaceutically acceptable carrier.

Preferably, the pharmaceutical composition of the present invention is suitable for oral or parenteral administration.

In a preferred embodiment, the pharmaceutical composition is useful for the treatment of cell proliferative disorders.

Further, the present invention concerns the use of a polycyclic compound of formula [I] for the preparation of pharmaceutical compositions.

Preferably, the use of a polycyclic compound of formula [I] according to the present invention is for the preparation of pharmaceutical compositions for the treatment of cell proliferative disorders.

More preferably, the use according to the present invention is for the preparation of pharmaceutical compositions for the treatment of cancer, and more preferably for the treatment of colorectal cancer, lung cancer, breast cancer, stomach cancer, cervical cancer or bladder cancer.

The present invention comprises also a method for treating a cell proliferative disorder comprising administering to a patient in need thereof a therapeutically effective amount of a polycyclic compound of formula [I].

Preferably, the present invention concerns a method wherein the cell proliferative disorder is cancer and more preferably, wherein the cancer is solid tumor and much more preferably colorectal cancer, lung cancer, breast cancer, stomach cancer, cervical cancer and bladder cancer.

Furthermore, the present invention concerns a process for producing polycyclic compounds of the formula [I],

[I]

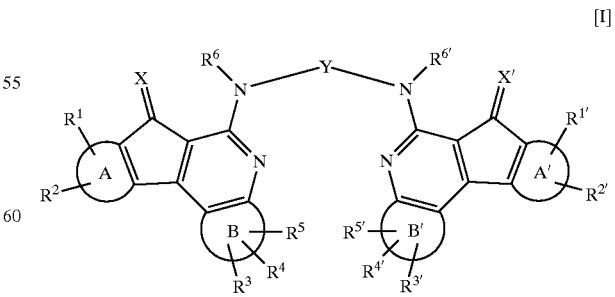

wherein ring A, ring B, $R^1$, $R^2$, $R^3$, $R^4$, $R^5$, $R^6$, Y, ring A', ring B', $R^{1'}$, $R^{2'}$, $R^{3'}$, $R^{4'}$, $R^{5'}$ and $R^{6'}$ are the same as defined as above, and X and X' are O, which comprises reacting either two compounds of the formulae [VI], [VI'], [VII] or [VII'],

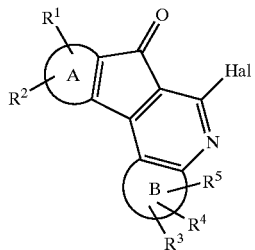
[VI]

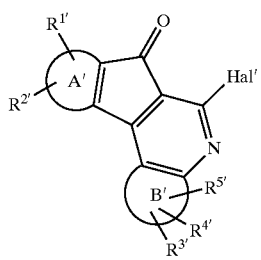
[VI']

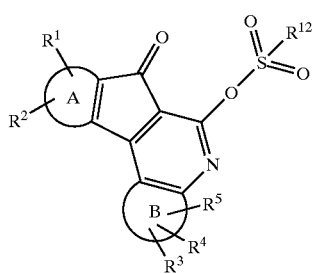
[VII]

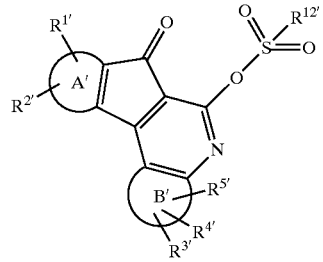
[VII']

wherein ring A, ring B, $R^1$, $R^2$, $R^3$, $R^4$, $R^5$, ring A', ring B', $R^{1'}$, $R^{2'}$, $R^{3'}$, $R^{4'}$ and $R^{5'}$ are the same as defined as above; Hal and Hal' are the same or different halogen atoms; and $R^{12}$ and $R^{12'}$ are independently $(C_1-C_5)$-alkyl, $(C_1-C_5)$-halogenalkyl or aryl, with a compound of the formula [VIII],

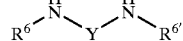
[VIII]

wherein $R^6$, Y and $R^{6'}$ are the same as defined as above.

In more detail, the compounds of the present invention can be prepared as follows:

Process 1

Key intermediates, compounds 6, 7, 6' and 7' can be prepared according to the following Flow Chart 1:

The definitions of the symbols in Flow Chart 1 are as follows. Hal and Hal' are the same or different halogen atoms. $R^{11}$ and $R^{11'}$ are the same or different $(C_1-C_5)$-alkyl such as methyl, ethyl, propyl and butyl. $R^{1a}$ and $R^{2a}$ are $R^1$ and $R^2$, respectively, or protected $R^1$ and protected $R^2$ which can be converted to $R^1$ and $R^2$, respectively, by methods known in the art. $R^{1a'}$ and $R^{2a'}$ are $R^{1'}$ and $R^{2'}$, respectively, or protected $R^{1'}$ and protected $R^{2'}$ which can be converted to $R^{1'}$ and $R^{2'}$, respectively, by methods known in the art. $R^{12}$ and $R^{12'}$ are independently $(C_1-C_5)$-alkyl such as methyl, $(C_1-C_5)$-halogenoalkyl such as trifluoro-methyl or aryl such as p-methylphenyl and phenyl.

Flow Chart 1: Preparation of key intermediates

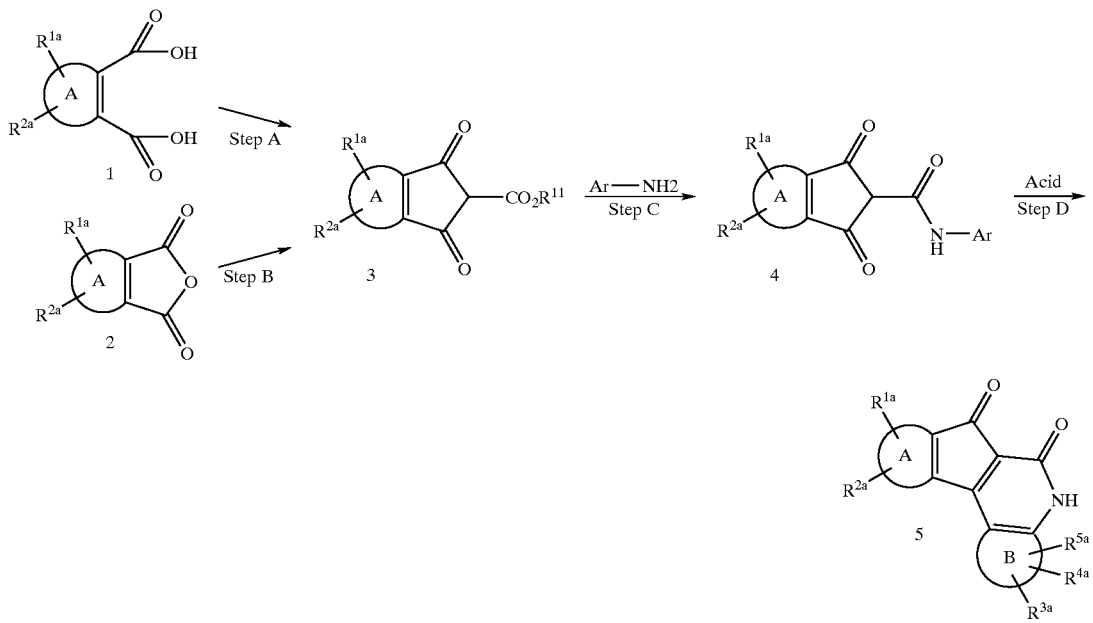

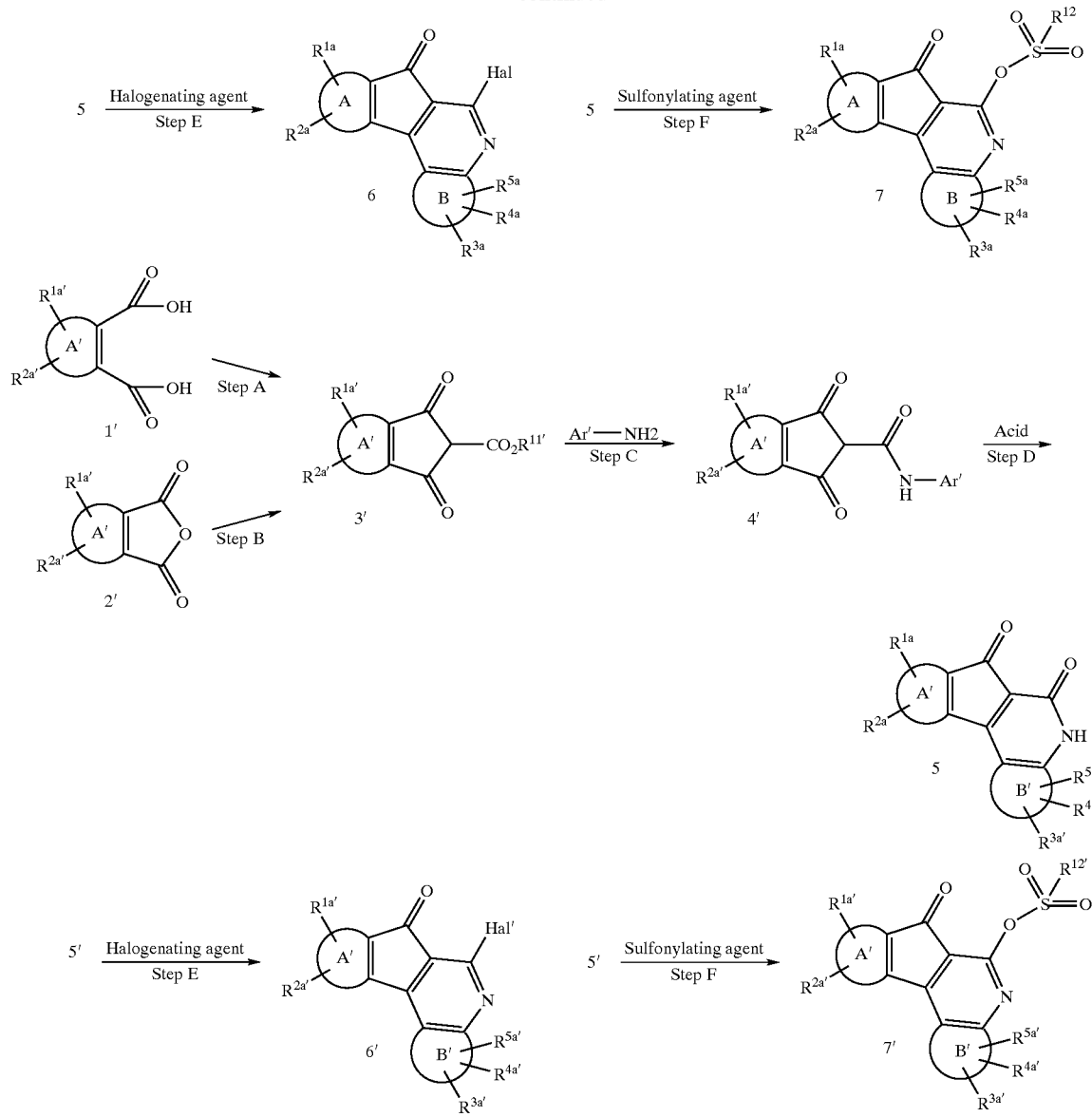

$R^{3a}$, $R^{4a}$ and $R^{5a}$ are the same as $R^3$, $R^4$ and $R^5$ defined above, respectively; or protected $R^3$, protected $R^4$ and protected $R^5$ which can be easily converted to $R^3$, $R^4$ and $R^5$, respectively, by methods known in the art. $R^{3a'}$, $R^{4a'}$ and $R^{5a'}$ are the same as $R^{3'}$, $R^{4'}$ and $R^{5'}$ defined above, respectively; or protected $R^{3'}$, protected $R^{4'}$ and protected $R^{5'}$ which can be easily converted to $R^{3'}$, $R^{4'}$ and $R^{5'}$, respectively, by methods known in the art. Ar—$NH_2$ means aniline derivatives which may be substituted by $R^{3a}$, $R^{4a}$ and $R^{5a}$. Ar'—$NH_2$ means aniline derivatives which may be substituted by $R^{3a'}$, $R^{4a'}$ and $R^{5a'}$. The definitions of ring A, ring B, ring A' and ring B' are the same as defined above.

For example, typically, dicarboxylic acid 1 is converted into compound 3 by 1) refluxing compound 1 in acetic anhydride and then 2) treating the resulting acid an hydride with acetoacetic acid ester in the presence of a base such as triethylamine in acetic anhydride at room temperature (see, Robin D. Allan and Joyce Fong, Aust. J. Chem., Vol. 36, Pp. 1221–1226, 1983). Compound 3 can also be prepared from dicarboxylic acid anhydride 2 by treatment with acetoacetic acid ester and a base such as triethylamine in acetic anhydride at room temperature (see, Binder D., Monatshefte für Chemie, Vol. 105, Pp. 179–186, 1974). Compound 4 is obtained by heating compound 3 with Ar—$NH_2$ in an inert solvent such as toluene. The reaction temperature is from 40 to 160° C., preferably 80 to 110° C. The amide 4 can be cyclized to obtain polycyclic lactam 5 by heating compound 4 in an acid such as polyphosphoric acid, trifluoromethane sulfonic acid and sulfonic acid. The compound 5 can be halogenated by a halogenating reagent such as thionyl chloride, thionyl bromide, phosphorous oxychloride, phosphorous chloride and phosphorous bromide. The preferable temperature for this reaction ranges from room temperature to reflux, and most preferably 50 to 110° C. Thus, the key intermediate 6 can be synthesized. The compound 5 can be sulfonylated by treating 5 with a sulfonylating agent such as methanesulfonyl chloride, benzenesulfonyl chloride, p-toluenesulfonyl chloride and trifluoromethanesulfonic anhydride. Typically compound 5, the sulfonylating agent and a phase transfer catalyst such as tetrabutylammonium bromide are suspended in a mixture of an organic solvent such as dichloromethane and water containing a base such as sodium hydroxide, and the mixture is vigorously stirred for a few hours to a few days, typically overnight. Thus, the key intermediate 7 can be synthesized.

In case one of $R^{1a}$, $R^{2a}$, $R^{3a}$, $R^{4a}$ and $R^{5a}$ of compound 6 is alkoxy such as methoxy this alkoxy group can be cleaved by sulfuric acid at 160° C. to give a hydroxy derivative. The resulting phenol group can be further modified by methods known in the art. For example, when the phenol having the general formula 6 is treated with $(C_1-C_5)$-alkyl halide, aryl$(C_1-C_5)$-alkyl halide, $(C_3-C_5)$-alkenyl halide, $(C_4-C_7)$-cycloalkyl halide and $(C_3-C_7)$-cycloalkyl$(C_1-C_5)$-alkyl halide; $(C_1-C_5)$-alkoxy, aryl$(C_1-C_5)$-alkyloxy, $(C_3-C_5)$-alkenyloxy, $(C_4-C_7)$-cycloalkyloxy and $(C_3-C_7)$cycloalkyl, $(C_1-C_5)$-alkyloxy derivatives can be prepared, respectively.

Compounds 6' and 7' can also be prepared by the same methods starting from compounds 1' or 2'.

Active polycyclic compounds can be synthesized from the key intermediates 6, 7, 6' and 7' by reacting two of them with $NHR^6$—Y—$NHR^{6'}$ as shown in Flow Chart 2. The definitions of $R^6$, Y, $R^{6'}$ are the same as defined above.

Process 2

The definitions of the symbols in Flow Chart 2 are as follows. Hal and Hal' are the same or different halogen atoms. $R^{12}$ is $(C_1-C_5)$-alkyl such as methyl, $(C_1-C_5)$-halogen-alkyl such as trifluoromethyl or aryl such as p-methylphenyl and phenyl. $R^{12'}$ is $(C_1-C_5)$-alkyl such as methyl, $(C_1-C_5)$-halogenalkyl such as trifluoromethyl or aryl such as p-methylphenyl and phenyl. $R^{3a}$, $R^{4a}$ and $R^{5a}$ are the same as $R^3$, $R^4$ and $R^5$ defined above, respectively; or protected $R^3$, protected $R^4$ and protected $R^5$ which can be easily converted to $R^3$, $R^4$ and $R^5$, respectively, by methods known in the art. $R^{3a'}$, $R^{4a'}$ and $R^{5a'}$ are the same as $R^{3'}$, $R^{4'}$ and $R^{5'}$ defined above, respectively; or protected $R^{3'}$, protected $R^{4'}$ and protected $R^{5'}$ which can be easily converted to $R^{3'}$, $R^{4'}$ and $R^{5'}$, respectively, by methods known in the art. The definitions of ring A, ring B, $R^6$, Y, ring A', ring B' and $R^{6'}$ are the same as defined above.

Flow Chart 2: Modification of key intermediates.

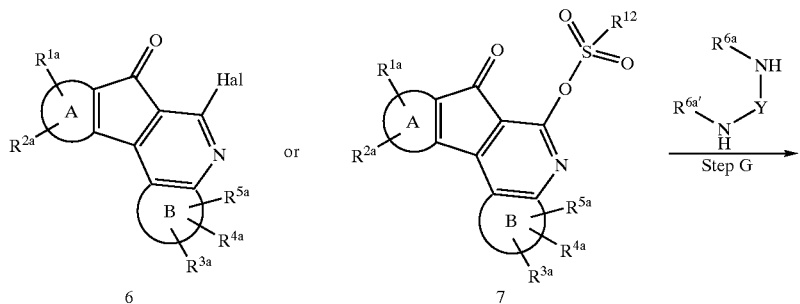

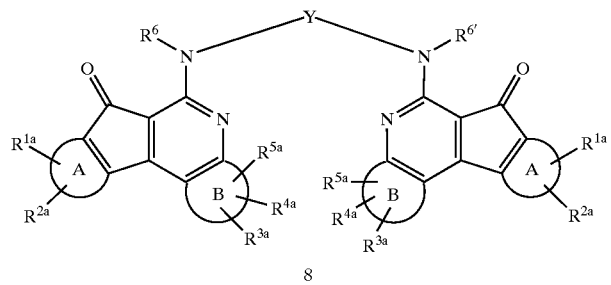

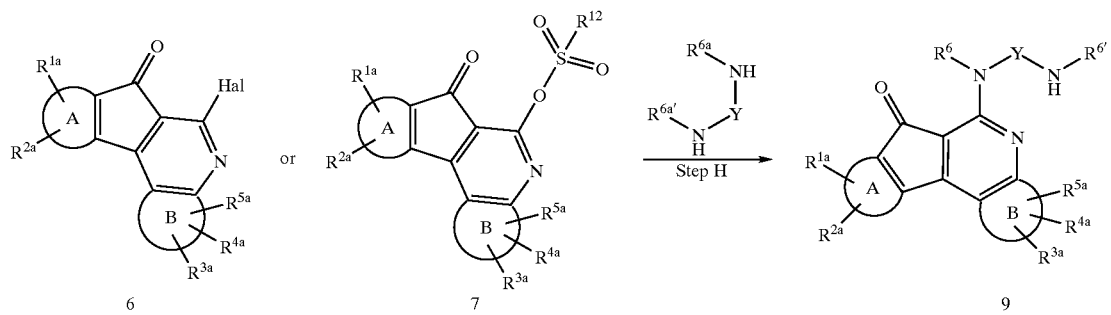

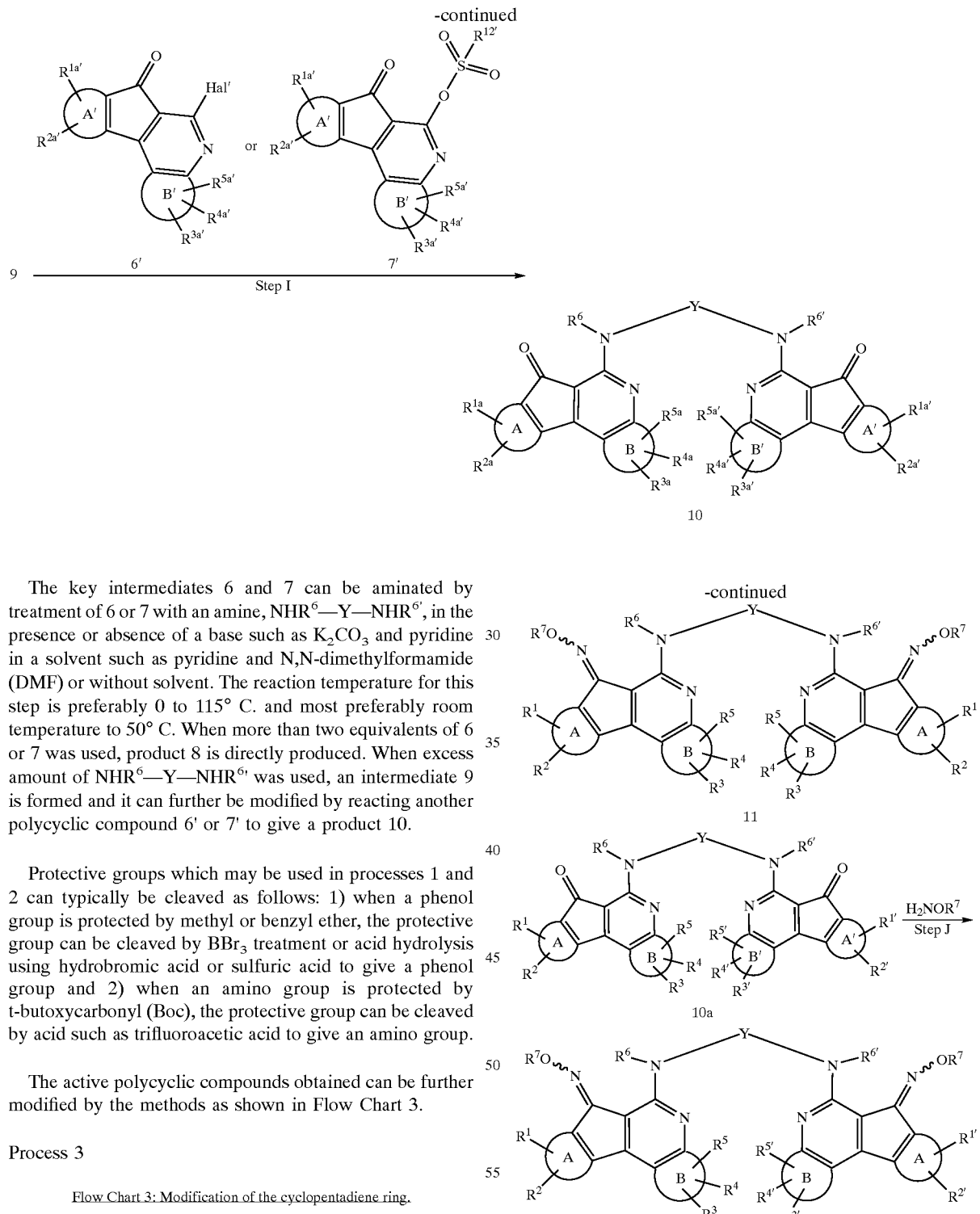

The key intermediates 6 and 7 can be aminated by treatment of 6 or 7 with an amine, NHR$^6$—Y—NHR$^{6'}$, in the presence or absence of a base such as K$_2$CO$_3$ and pyridine in a solvent such as pyridine and N,N-dimethylformamide (DMF) or without solvent. The reaction temperature for this step is preferably 0 to 115° C. and most preferably room temperature to 50° C. When more than two equivalents of 6 or 7 was used, product 8 is directly produced. When excess amount of NHR$^6$—Y—NHR$^{6'}$ was used, an intermediate 9 is formed and it can further be modified by reacting another polycyclic compound 6' or 7' to give a product 10.

Protective groups which may be used in processes 1 and 2 can typically be cleaved as follows: 1) when a phenol group is protected by methyl or benzyl ether, the protective group can be cleaved by BBr$_3$ treatment or acid hydrolysis using hydrobromic acid or sulfuric acid to give a phenol group and 2) when an amino group is protected by t-butoxycarbonyl (Boc), the protective group can be cleaved by acid such as trifluoroacetic acid to give an amino group.

The active polycyclic compounds obtained can be further modified by the methods as shown in Flow Chart 3.

Process 3

Ring A, ring B, R$_1$, R$_2$, R$_3$, R$_4$, R$_5$, R$_6$, R$_7$, Y, ring A', ring B', R$^{1'}$, R$^{2'}$, R$^{3'}$, R$^{4'}$, R$^{5'}$ and R$^{6'}$ have the same definitions as defined above. Compounds 8a and 10a are the same 8 and 10 in Flow Chart 2 wherein R$^{1a}$, R$^{2a}$, R$^{3a}$, R$^{4a}$, and R$^{5a}$ are the same as R$^1$, R$^2$, R$^3$, R$^4$ and R$^5$, respectively.

The ketone groups of the cyclopentadiene moieties can be modified by the reaction with oxime or various oxime-ethers ($H_2N$—O—$R^7$) in the absence or in the presence of an acid such as hydrochloric acid, hydrobromic acid and acetic acid in an appropriate solvent such as pyridine at an elevated temperature typically at about 80° C.

The manufacture of the pharmaceutically acceptable acid addition salts of the compound of formula [I] can be carried out by treating a free base of the compound represented by formula [I] with an acid in a manner known to the skilled artisan for salt formation. Examples of therapeutically acceptable acids useful in the above process are inorganic acids (e.g. hydrochloric acid, hydrobromic acid, phosphoric acid, nitric acid, sulfuric acid) and organic acids (e.g. oxalic acid, acetic acid, formic acid, trifluoroacetic acid, maleic acid, succinic acid, fumaric acid, tartaric acid, citric acid, salicylic acid, sorbic acid, lactic acid, methanesulfonic acid). Moreover, the compounds of formula [I] can be converted into the hydrates or solvates and their salts by various methods known to those skilled in the art.

The polycyclic compounds of formula [I] show strong anti-tumor activity against various tumor cell lines. This anti-tumor activity indicates that the compounds of formula [I] and pharmaceutically acceptable salts thereof are anti-tumor agents.

The polycyclic compounds of formula [I] and pharmaceutically acceptable salts thereof are very strong cytotoxic agents. They are active against a variety of cell lines including colon cancer cell lines, non-small cell lung cancer cell lines, pancreatic cancer cell lines and gastric cancer cell lines, etc.

Thus, the polycyclic compounds of the present invention are useful for the treatment of cancer. Accordingly, the present invention comprises the use of the above compounds for the manufacture of pharmaceutical compositions for the treatment of cancer and the corresponding pharmaceutical compositions which comprise a polycyclic compound as defined above and a pharmaceutically acceptable carrier.

For example, they are useful in treating leukemia, lymphoma, myeloma, prostate cancer, breast cancer, hepatoma, glioblastoma, ovarian cancer, melanoma, lung cancer, colorectal cancer, pancreatic cancer, gastric cancer, etc.

The anti-tumor activity of the polycyclic compounds of the present invention can be demonstrated as follows:

Determination of the Anti-tumor Activity

Anti-proliferative Activity Assay

A single suspension of tumor cells was inoculated to the serially diluted 96-well microtestplate. Then the testplate was incubated in the 5% $CO_2$ ambience at 37° C. for 4 days (2–3×$10^3$ cells/well). The degree of cell growth in a monolayer was measured by using WST-8 (Dojindo, Japan). $IC_{50}$ values of the polycyclic compounds directed against tumor cells were calculated as the concentration of drug yielding 50% OD of the control growth.

The anti-tumor activity of polycyclic compounds of the formula [I] against in vitro growth of HCT116 cell line (colorectal cancer) is summarized in Table 1.

The reference compound has been disclosed in EP 0713870 (1996) as an anti-tumor agent.

TABLE 1

Anti-tumor activity in vitro

| Compound | HCT116 (colorectal cancer) - $IC_{50}$ (nM) |
|---|---|
| 6-{2-[methyl-(3-{methyl-[2-(7-oxo-7H-5,9-diaza-benzo[c]fluoren-6-ylamino)-ethyl]-amino}-propyl)-amino]-ethylamino}-5,9-diaza-benzo[c]fluoren-7-one | 0.64 |
| 3-chloro-6-{2-[(3-{[2-(3-chloro-7-oxo-7H-5,9-diaza-benzo[c]fluoren-6-ylamino)-ethyl]-methyl-amino}-propyl)-methyl-amino]-ethylamino}-5,9-diaza-benzo[c]fluoren-7-one | 0.02 |
| 6-{2-[methyl-(3-{methyl-[2-(7-oxo-7H-5,10-diaza-benzo[c]fluoren-6-ylamino)-ethyl]-amino}-propyl)-amino]-ethylamino}-5,10-diaza-benzo[c]fluoren-7-one | 0.3 |
| 6-{2-[methyl-(3-{methyl-[2-(7-oxo-7H-5,10-diaza-benzo[c]fluoren-6-ylamino)-ethyl]-amino}-propyl)-amino]-ethylamino}-5,9-diaza-benzo[c]fluoren-7-one | 0.13 |
| 3-methoxy-6-{2-[methyl-(3-{methyl-[2-(7-oxo-7H-5,9-diaza-benzo[c]fluoren-6-ylamino)-ethyl]-amino}-propyl)-amino]-ethylamino}-5,9-diaza-benzo[c]fluoren-7-one | 0.08 |
| Reference compound: 6-(2-dimethylamino-ethylamino)-3-hydroxy-7H-indeno[2,1-c]quinolin-7-one | 12 |

The acute toxicity ($LD_{50}$) of the polycyclic compounds of the present invention was examined by intravenous administration in mice. The $LD_{50}$ value of the compounds was more than 90 mg/kg.

For clinical use, the polycyclic compounds of the formula [I], their prodrugs, or salt forms thereof and the like can be administered alone, but will generally be administered in pharmaceutical admixture formulated as appropriate to the particular use and purpose desired, by mixing excipient, binding agent, lubricant, disintegrating agent, coating material, emulsifier, suspending agent, solvent, stabilizer, absorption enhancer and/or ointment base. The admixture can be used for oral, injectable, rectal or topical administration.

In more detail, as mentioned earlier, pharmaceutical compositions containing a compound of formula [I] or its prodrug are also an object of the present invention, as is a process for the manufacture of such pharmaceutical compositions, whose process comprises bringing one or more compounds of formula [I] and, if desired, one or more other therapeutically valuable substances into a galenical administration form.

The pharmaceutical compositions may be administered orally, for example in the form of tablets, coated tablets, dragées, hard or soft gelatine capsules, solutions, emulsions or suspensions. Administration can also be carried out rectally, for example using suppositories; locally or percutaneously, for example using ointments, creams, gels or solutions; or parenterally, for example using injectable solutions.

For the preparation of tablets, coated tablets, dragées or hard gelatine capsules the compounds of the present invention may be admixed with pharmaceutically inert, inorganic or organic excipients. Examples of suitable excipients for tablets, dragées or hard gelatine capsules include lactose, maize starch or derivatives thereof, talc or stearic acid or salts thereof.

Suitable excipients for use with soft gelatine capsules include, for example, vegetable oils, waxes, fats, semi-solid or liquid polyols, etc. According to the nature of the active ingredients, it may however be the case that no excipient is needed at all for soft gelatine capsules.

For the preparation of solutions and syrups, excipients which may be used include for example water, polyols, saccharose, invert sugar and glucose.

For injectable solutions, excipients which may be used include, for example, water, alcohols, polyols, glycerin, and vegetable oils.

For suppositories, and local or percutaneous application, excipients which may be used include, for example, natural or hardened oils, waxes, fats and semi-solid or liquid polyols.

The pharmaceutical compositions may also contain preserving agents, solubilizing agents, stabilizing agents, wetting agents, emulsifiers, sweeteners, colorants, odorants, salts for the variation of osmotic pressure, buffers, coating agents or antioxidants. They may also contain other therapeutically valuable agents.

In summary, a pharmaceutical formulation for oral administration may be granule, tablet, sugar coated tablet, capsule, pill, suspension or emulsion, which for parenteral injection, for example, intravenously, intramuscularly or subcutaneously, may be used in the form of a sterile aqueous solution which may contain other substances, for example, salts or glucose to make the solution isotonic. The antitumor agent can also be administered in the form of a suppository or pessary, or they may be applied topically in the form of a lotion, solution, cream, ointment or dusting powder.

The daily dosage level of the polycyclic compounds of formula [I] is from 5 to 2,000 mg/m² when administered by either the oral or parenteral route. Thus, tablets or capsules can contain from 5 mg to 1,000 mg of active compound for administration singly or two or more at a time as appropriate. In any event the actual dosage can be weight and response of the particular patient.

The following examples illustrate the preferred methods for the preparation of the compounds of the present invention, which are not intended to limit the scope of the invention thereto.

EXAMPLES

Reference Example 1

Preparation of 6-chloro-3-methoxy-5,10-diaza-benzo[c]fluoren-7-one (Reference Example 1c-1) and 6-chloro-3-methoxy-5,9-diaza-benzo[c]fluoren-7-one (Reference Example 1c-2)

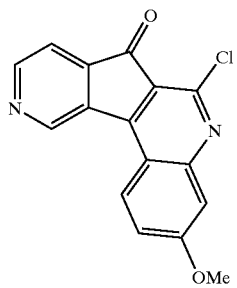

1c-1

-continued

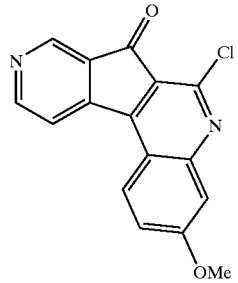

1c-2 a) Preparation of 5,7-dioxo-6,7-dihydro-5H-[2]pyrindine-6-carboxylic acid (3-methoxy-phenyl)-amide 5,7-Dioxo-6,7-dihydro-5H-[2]pyrindine-6-carboxylic acid ethyl ester (18 g) (see, Robin D. Allan and Joyce Fong, Aust. J. Chem., Vol. 36, pp. 1221–1226, 1983), m-anisidine (17.7 ml) and acetic acid (9 ml) were suspended in toluene (1,000 ml). This mixture was refluxed for 110 minutes under nitrogen. The mixture was cooled to room temperature and the precipitate was collected with suction. The precipitate was washed with toluene and dichloromethane and dried under reduced pressure to give a brown powder (21.6 g).

ESI-MS: m/z 297 (MH$^+$); $^1$H-NMR (DMSO-d6): δ 3.74 (3H, s), 6.54 (1H, dd, J=8.5 Hz, J=2.5 Hz), 7.00 (1H, bd, J=8.5 Hz), 7.17 (1H, t, J=8.5 Hz), 7.42 (1H, t-like, J=ca 2.5 Hz), 7.73 (1H, d, 5 Hz), 8.71 (1H, s), 8.91 (1H, d, J=5 Hz), 10.65 (1H, brs).

b) Preparation of a Mixture of 3-methoxy-5H-5,9-diaza-benzo[c]fluorene-6,7-dione and 3-methoxy-5H-5,10-diaza-benzo[c]fluorene-6,7-dione 5,7-Dioxo-6,7-dihydro-5H-[2]pyrindine-6-carboxylic acid (3-methoxy-phenyl)-amide (11 g) obtained above was triturated in polyphosphoric acid (Merck: 150 g) and the mixture was stirred at 110° C. for two hours under argon gas. To the cooled mixture were added ice (400 g) and ammonia water to adjust the pH 7. Dark brown precipitate was collected with suction and washed with water to give a mixture (9.85 g) of 3-methoxy-5H-5,9-diaza-benzo[c]fluorene-6,7-dione and 3-methoxy-5H-5,10-diaza-benzo[c]fluorene-6,7-dione.

ESI-MS: m/z 279 (MH$^+$).

c) Preparation of 6-chloro-3-methoxy-5,10-diaza-benzo[c]fluoren-7-one (Reference Example 1c-1) and 6-chloro-3-methoxy-5,9-diaza-benzo[c]fluoren-7-one (Reference Example 1c-2)

The mixture of 3-methoxy-5H-5,9-diaza-benzo[c]fluorene-6,7-dione and 3-methoxy-5H-5,10-diaza-benzo[c]fluorene-6,7-dione (8.77 g) obtained above was suspended in phosphorus oxychloride (359 g) and stirred at 60° C. for three days. Excess phosphorus oxychloride was evaporated under reduced pressure. The residue was treated with ice water and saturated sodium hydrogen carbonate to adjust the pH about 7. Black precipitate was collected with suction and washed water. The precipitate was purified by silica gel column chromatography developed by dichloromethane-methanol-trifluoroacetic acid (200:2:1) and by dichloromethane-methanol-trifluoroacetic acid (200:4:1). This chromatography gave two yellow bands. The first band was collected and evaporated. The residue was treated with methanol to give less polar isomer (1.72 g), 6-chloro-3-methoxy-5,10-diaza-benzo[c]fluoren-7-one (Reference Example 1c-1) as a yellow powder. The second band was collected and evaporated. The residue was treated with methanol to give more polar isomer (1.86 g), 6-chloro-3-methoxy-5,9-diaza-benzo[c]fluoren-7-one (Reference Example 1c-2) as a yellow powder.

6-Chloro-3-methoxy-5,10-diaza-benzo[c]fluoren-7-one (Reference Example 1c-1):

ESI-MS: m/z 297 (MH$^+$); $^1$H-NMR (DMSO-d$_6$): δ 4.03 (3H, s), 7.47 (1H, dd, J=9 Hz, 2.5 Hz), 7.54 (1H, d, J=2.5 Hz), 7.74 (1H, d, J=4.5 Hz), 8.78 (1H, d, J=9 Hz), 8.96 (1H, d, 4.5 Hz), 9.73 (1H, s).

6-Chloro-3-methoxy-5,9-diaza-benzo[c]fluoren-7-one (Reference Example 1c-2):

ESI-MS: m/z 297 (MH$^+$); $^1$H-NMR (DMSO-d6): δ 4.02 (3H, s), 7.51 (1H, dd, J=9 Hz, 2.5 Hz), 7.55 (1H, d, J=2.5 Hz), 8.50 (1H, d, J=4.5 Hz), 8.73 (1H, d, J=9 Hz), 8.93 (1H, s), 9.00 (1H, d, 4.5 Hz).

Reference Example 2

Preparation of toluene-4-sulfonic acid 3-methoxy-4-methyl-7-oxo-7H-5,10-diaza-benzo[c]fluoren-6-yl ester (Reference Example 2c-1) and toluene-4-sulfonic acid 3-methoxy-4-methyl-7-oxo-7H-5,9-diaza-benzo[c]fluoren-6-yl ester (Reference Example 2c-2)

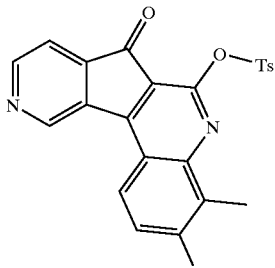

2c-1

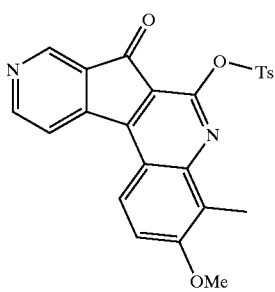

2c-2 a) Preparation of 5,7-dioxo-6,7-dihydro-5H-[2]pyrindine-6-carboxylic acid (3-methoxy-4-methyl-phenyl)-amide 5,7-Dioxo-6,7-dihydro-5H-[2]pyrindine-6-carboxylic acid ethyl ester (975 mg) (see, Robin D. Allan and Joyce Fong, Aust. J. Chem., Vol. 36, pp. 1221–1226, 1983), 3-methoxy-2-methyl-phenylamine (750 mg) and acetic acid (0.4 ml) were suspended in toluene (30 ml). This mixture was refluxed for one hour under nitrogen. The mixture was cooled to room temperature and the precipitate was collected with suction. The precipitate was washed with toluene and dichloromethane and dried under reduced pressure to give an orange powder (1.1 g).

ESI-MS: m/z 311 (MH$^+$); $^1$H-NMR (DMSO-d6+ triethylamine (1 eq.)): δ 2.18 (3H, s), 3.77 (3H, s), 6.60 (1H, d, J=8 Hz), 7.05 (1H, t, J=8 Hz), 7.32 (1H, dd, J=4.5 Hz, J=1 Hz), 7.99 (1H, d, J=8 Hz), 8.50 (1H, d, J=1 Hz), 8.71 (1H, d, J=4.5 Hz), 10.6 (1H, s).

b) Preparation of a mixture of 3-methoxy-4-methyl-5H-5,10-diaza-benzo[c]fluorene-6,7-dione and 3-methoxy-4-methyl-5H-5,9-diaza-benzo[c]fluorene-6,7-dione 5,7-Dioxo-6,7-dihydro-5H-[2]pyrindine-6-carboxylic acid (3-methoxy-4-methyl-phenyl)-amide (1 g) obtained above was triturated in polyphosphoric acid (Merck: 10 g) and the mixture was stirred at 120° C. for two hours under argon gas. To the cooled mixture was added ice (400 g) and ammonia water to adjust the pH 7. Dark brown precipitate was collected with suction and washed with water to give a mixture (860 mg) of 3-methoxy-4-methyl-5H-5,10-diaza-benzo[c]fluorene-6,7-dione and 3-methoxy-4-methyl-5H-5,9-diaza-benzo[c]fluorene-6,7-dione.

ESI-MS: m/z 293 (MH$^+$)

c) Preparation of toluene-4-sulfonic acid 3-methoxy-4-methyl-7-oxo-7H-5,10-diaza-benzo[c]fluoren-6-yl ester (Reference Example 2c-1) and toluene-4-sulfonic acid 3-methoxy-4-methyl-7-oxo-7H-5,9-diaza-benzo[c]fluoren-6-yl ester (Reference Example 2c-2)

A mixture of the mixture of 3-methoxy-4-methyl-5H-5,10-diaza-benzo[c]fluorene-6,7-dione and 3-methoxy-4-methyl-5H-5,9-diaza-benzo[c]fluorene-6,7-dione (688 mg) obtained above, p-toluenesulfonyl chloride (718 mg), tetrabutylammonium bromide (1.38 g), 0.025 mol sodium hydroxide solution (140 ml), and dichloromethane (280 ml) was stirred vigorously at room temperature for 22 hours. The organic layer was separated and the water layer was extracted with dichloromethane (80 ml). The organic layer combined was evaporated under reduced pressure. The residue was triturated with methanol (150 ml) to give brown powder. The powder was purified by silica gel column chromatography developed by dichloromethane-methanol-trifluoroacetic acid (300:1). This chromatography gave two yellow bands. The first band was collected and evaporated. The residue was treated with methanol to give less polar isomer (300 mg), toluene-4-sulfonic acid 3-methoxy-4-methyl-7-oxo-7H-5,10-diaza-benzo[c]fluoren-6-yl ester (Reference Example 2c-1) as a yellow powder. The second band was collected and evaporated. The residue was treated with methanol to give more polar isomer (250 mg), toluene-4-sulfonic acid 3-methoxy-4-methyl-7-oxo-7H-5,9-diaza-benzo[c]fluoren-6-yl ester (Reference Example 2c-2) as a yellow powder.

Toluene-4-sulfonic acid 3-methoxy-4-methyl-7-oxo-7H-5,10-diaza-benzo[c]fluoren-6-yl ester (Reference Example 2c-1):

ESI-MS: m/z 447 (MH$^+$); $^1$H-NMR (CDCl$_3$): δ 2.40 (3H, s), 2.47 (3H, s), 4.06 (3H, s), 7.39 (2H, d, J=8.5 Hz), 7.47 (1H, d, J=9 Hz), 7.66 (1H, dd, J=4.5 Hz, 1Hz), 8.09 (2H, d, J=8.5 Hz), 8.32 (1H, d, J=9 Hz), 8.90 (1H, d, J=4.5 Hz), 9.42 (1H, d, J=1 Hz).

Toluene-4-sulfonic acid 3-methoxy-4-methyl-7-oxo-7H-5,9-diaza-benzo[c]fluoren-6-yl ester (Reference Example 2c-2):

ESI-MS: m/z 447 (MH$^+$); $^1$H-NMR (CDCl$_3$): δ 2.43 (3H, s), 2.48 (3H, s), 4.06 (3H, s), 7.40 (2H, d, J=8.5 Hz), 7.46 (1H, d, J=9.5 Hz), 7.98 (1H, dd, J=5 Hz, 1 Hz), 8.09 (2H, d, J=8.5 Hz), 8.32 (1H, d, J=9.5 Hz), 8.93 (1H, d, J=5 Hz), 8.99 (1H, d, J=1 Hz).

Reference Example 3

Preparation of toluene-4-sulfonic acid 3-methoxy-9-methyl-7-oxo-7H-5,10-diaza-benzo[c]fluoren-6-yl ester

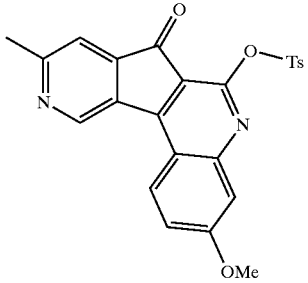

a) Preparation of 3-methyl-5,7-dioxo-6,7-dihydro-5H-[2]pyrindine-6-carboxylic acid ethyl ester 6-Methyl-pyridine-3,4-dicarboxylic acid (440 mg) (see, Emil J. Moriconi and Francis A. Spano, J. Am. Chem. Soc., Vol. 86, pp. 38–46, 1964) was suspended in acetic anhydride (10 ml) and the mixture was refluxed for 10 minutes. Ethyl acetoacetate (0.325 ml) and triethylamine (0.745 ml) were dropwise added to the mixture at room temperature and the mixture was stirred overnight. The mixture was concentrated to dryness and purified by silica gel column chromatography developed by dichloromethane and by dichloromethane-methanol (15:1). The desired compound was obtained as a dark red oil which contained 1 equivalent of triethylamine.

ESI-MS: m/z 234 (MH$^+$); $^1$H-NMR (CDCl$_3$): δ 1.26–1.38 (15H, m), 2.63 (3H, s), 3.28 (6H, q, J=3.3 Hz), 4.22 (2H, q, J=4.2 Hz), 7.29 (1H, s), 8.58 (1H, s).

b) Preparation of 3-methyl-5,7-dioxo-6,7-dihydro-5H-[2]pyrindine-6-carboxylic acid (3-methoxy-phenyl)-amide In a similar manner to Reference Example 1a, 3-methyl-5,7-dioxo-6,7-dihydro-5H-[2]pyrindine-6-carboxylic acid (3-methoxy-phenyl)-amide was obtained starting from the compound of Reference Example 3a. The desired product was obtained as a yellowish red powder.

ESI-MS: m/z 311 (MH$^+$); $^1$H-NMR (DMSO-d6): δ 2.54 (3H, s), 3.74 (3H, s), 6.51 (1H, ddd, J=8.3 Hz, 2.3 Hz, 1.0 Hz), 6.99 (1H, ddd, J=7.9 Hz, 1.98 Hz, 1.0 Hz), 7.13 (1H, t-like, J=7.9 Hz), 7.18 (1H, d, J=1 Hz), 7.41 (1H, t-like, J=2.3 Hz), 8.35 (1H, d, J=1.0 Hz), 10.80 (1H, s).

c) Preparation of a mixture of 3-methoxy-9-methyl-5H-5,10-diaza-benzo[c]fluorene-6,7-dione and 3-methoxy-10-methyl-5H-5,9-diaza-benzo[c]fluorene-6,7-dione In a similar manner to Reference Example 1b, a mixture of 3-methoxy-9-methyl-5H-5,10-diaza-benzo[c]fluorene-6,7-dione and 3-methoxy-10-methyl-5H-5,9-diaza-benzo[c]fluorene-6,7-dione was obtained as a dark brown solid starting from the compound of Reference Example 3b.

ESI-MS: m/z 293 (MH$^+$).

d) Preparation of toluene-4-sulfonic acid 3-methoxy-9-methyl-7-oxo-7H-5,10-diaza-benzo[c]fluoren-6-yl ester In a similar manner to Reference Example 2c, toluene-4-sulfonic acid 3-methoxy-9-methyl-7-oxo-7H-5,10-diaza-benzo[c]fluoren-6-yl ester was obtained starting from the compound of Reference Example 3c. The desired product was obtained as a yellow powder.

ESI-MS: m/z 447 (MH$^+$); $^1$H-NMR (CDCl$_3$): δ 2.48 (3H, s), 2.71 (3H, s), 4.02 (3H, s), 7.35–7.38 (2H, m), 7.44 (2H, d, J=5.9 Hz), 7.49 (1H, s), 8.13 (2H, d, J=5.9 Hz), 8.29 (1H, d, J=6.8 Hz), 9.24 (1H, s).

Reference Example 4

Preparation of toluene-4-sulfonic acid 3-methoxy-8-methyl-7-oxo-7H-5,9-diaza-benzo[c]fluoren-6-yl ester

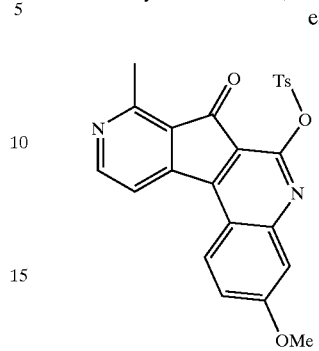

a) Preparation of 1-methyl-5,7-dioxo-6,7-dihydro-5H-[2]pyrindine-6-carboxylic acid ethyl ester In a similar manner to Reference Example 3a, 1-methyl-5,7-dioxo-6,7-dihydro-5H-[2]pyridine-6-carboxylic acid ethyl ester was obtained starting from 2-methyl-pyridine-3,4-dicarboxylic acid (see, Emil J. Moriconi and Francis A. Spano, J. Am. Chem. Soc., Vol. 86, pp. 38–46, 1964). The desired product was obtained as a red orange powder.

ESI-MS: m/z 234 (MH$^+$); $^1$H-NMR (CDCl$_3$): δ 1.35 (3H, t, J=7.3 Hz), 2.81 (3H, s), 4.21 (2H, q, J=7.3 Hz), 7.29 (1H, d, J=4.6 Hz), 8.53 (1H, d, J=4.6 Hz).b) Preparation of 1-methyl-5,7-dioxo-6,7-dihydro-5H-[2]pyrindine-6-carboxylic acid (3-methoxy-phenyl)-amide b) Preparation of 1-methyl-5,7-dioxo-6,7-dihydro-5H-[2]pyrindine-6-carboxylic acid (3-methoxy-phenyl)-amide In a similar manner to Reference Example 1a, 1-methyl-5,7-dioxo-6,7-dihydro-5H-[2]pyrindine-6-carboxylic acid (3-methoxy-phenyl)-amide was obtained starting from the compound of Reference Example 4a. The desired product was obtained as an orange powder.

ESI-MS: m/z 311 (MH$^+$); $^1$H-NMR (DMSO-d6): δ 2.88 (3H, s), 3.74 (3H, s), 6.54 (1H, d, J=8.3 Hz), 7.02 (1H, d, J=7.9 Hz), 7.16 (1H, dd, J=7.9 Hz, 8.3 Hz), 7.41 (1H, brs), 7.70 (1H, d, J=5.3 Hz), 8.85 (1H, d, J=5.3 Hz), 10.62 (1H, s).

c) Preparation of a mixture of 3-methoxy-8-methyl-5H-5,9-diaza-benzo[c]fluorene-6,7-dione and 3-methoxy-11-methyl-5H-5,10-diaza-benzo[c]fluorene-6,7-dione In a similar manner to Reference Example 1b, a mixture of 3-methoxy-8-methyl-5H-5,9-diaza-benzo[c]fluorene-6,7-dione and 3-methoxy-11-methyl-5H-5,10-diaza-benzo[c]fluorene-6,7-dione was obtained as a dark brown solid starting from the compound of Reference Example 4b.

ESI-MS: m/z 293 (MH$^+$).

d) Preparation of toluene-4-sulfonic acid 3-methoxy-8-methyl-7-oxo-7H-5,9-diaza-benzo[c]fluoren-6-yl ester In a similar manner to Reference Example 2c, toluene-4-sulfonic acid 3-methoxy-8-methyl-7-oxo-7H-5,9-diaza-benzo[c]fluoren-6-yl ester was obtained as a yellow powder starting from the compound of Reference Example 4c.

ESI-MS: m/z 447 (MH$^+$); $^1$H-NMR (CDCl$_3$): δ 2.49 (3H, s), 2.90 (3H, s), 4.01 (3H, s), 7.00–7.38 (2H, m), 7.43 (2H, d, J=7.9 Hz), 7.85 (1H, d, J=4.9 Hz), 8.15 (2H, d, J=7.9 Hz), 8.33 (1H, d, J=9.9 Hz), 8.79 (1H, d, J=4.9 Hz).

Reference Example 5

Preparation of toluene-4-sulfonic acid 11-chloro-3-methoxy-4-methyl-7-oxo-7H-5,10-diaza-benzo[c]fluoren-6-yl ester

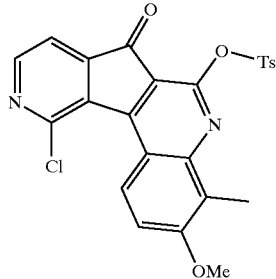

a) Preparation of 1-chloro-5,7-dioxo-6,7-dihydro-5H-[2]pyrindine-6-carboxylic acid ethyl ester In a similar manner to Reference Example 3a, 1-chloro-5,7-dioxo-6,7-dihydro-5H-[2]pyrindine-6-carboxylic acid ethyl ester was obtained starting from 2-chloro-pyridine-3,4-dicarboxylic acid (see, Florence Mongin, Francois Trecourt and Guy Queguiner, Tetrahedron Lett., Vol. 40, pp. 5483–5486, 1999). The desired product was obtained as a yellow powder.

ESI-MS: m/z 254 (MH$^+$); $^1$H-NMR (DMSO-d6): δ 1.18 (3H, t, J=6.9 Hz), 4.02 (2H, q, J=6.9 Hz), 7.33 (1H, d, J=4.3 Hz), 8.49 (1H, d, J=4.3 Hz).

b) Preparation of toluene-4-sulfonic acid 11-chloro-3-methoxy-4-methyl-7-oxo-7H-5,10-diaza-benzo[c]fluoren-6-yl ester In a similar manner to Reference Examples 2a–2c, toluene-4-sulfonic acid 11-chloro-3-methoxy-4-methyl-7-oxo-7H-5,10-diaza-benzo[c]fluoren-6-yl ester was obtained starting from 1-chloro-5,7-dioxo-6,7-dihydro-5H-[2]pyrindine-6-carboxylic acid ethyl ester (the compound of Reference Example 5a) and 3-methoxy-2-methyl-phenylamine. The desired product was obtained as an orange powder.

ESI-MS: m/z 481 (MH$^+$); $^1$H-NMR (CDCl$_3$): δ 2.40 (3H, s), 2.47 (3H, s), 4.06 (3H, s), 7.39 (2H, d, J=8 Hz), 7.41 (1H, d, J=10 Hz), 7.64 (1H, d, J=4.5 Hz), 8.07 (2H, d, J=8 Hz), 8.67 (1H, d, J=4.5 Hz), 9.17 (1H, d, J=10 Hz).

Reference Example 6

Preparation of toluene-4-sulfonic acid 7-oxo-7H-5,10-diaza-benzo[c]fluoren-6-yl ester (Reference Example 6c-1) and toluene-4-sulfonic acid 7-oxo-7H-5,9-diaza-benzo[c]fluoren-6-yl ester (Reference Example 6c-2)

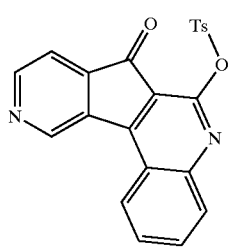

6c-1

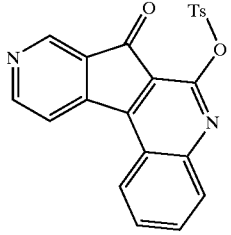

6c-2 a) Preparation of 5,7-dioxo-6,7-dihydro-5H-[2]pyrindine-6-carboxylic acid phenylamide In a similar manner to Reference Example 1a, 5,7-dioxo-6,7-dihydro-5H-[2]pyrindine-6-carboxylic acid phenylamide was obtained starting from 5,7-dioxo-6,7-dihydro-5H-[2]pyrindine-6-carboxylic acid ethyl ester and aniline. The desired product was obtained as a brownish orange powder.

ESI-MS: m/z 267 (MH$^+$); $^1$H-NMR (DMSO-d6): δ 6.93 (1H, t, J=7.3 Hz), 7.26 (2H, t-like, 7.3 Hz), 7.33 (1H, dd, J=1.4 Hz, 4.6 Hz), 7.59 (2H, d, J=7.3 Hz), 8.51 (1H, d, J=1.4 Hz), 8.72 (1H, d, J=4.6 Hz), 10.78 (1H, brs).

b) Preparation of a mixture of 5H-5,9-diaza-benzo[c]fluorene-6,7-dione and 3-methoxy-11-methyl-5H-5,10-diaza-benzo[c]fluorene-6,7-dione 5,7-Dioxo-6,7-dihydro-5H-[2]pyrindine-6-carboxylic acid phenylamide (1.33 g) obtained above was dissolved in trifluoromethanesulfonic acid (7 ml). The mixture was stirred at 100° C. for 2 days. To the cooled mixture was added ice (40 g). Dark brown precipitate was collected with suction and washed with sodium bicarbonate solution and water subsequently to give a mixture (1.2 g) of 5H-5,9-diaza-benzo[c]fluorene-6,7-dione and 3-methoxy-11-methyl-5H-5,10-diaza-benzo[c]fluorene-6,7-dione.

ESI-MS: m/z 249 (MH$^+$).

c) Preparation of toluene-4-sulfonic acid-7-oxo-7H-5,10-diaza-benzo[c]fluoren-6-yl ester (Reference Example 6c-1) and toluene-4-sulfonic acid 7-oxo-7H-5,9-diaza-benzo[c]fluoren-6-yl ester (Reference Example 6c-2)

In a similar manner to Reference Example 2c, toluene-4-sulfonic acid 7-oxo-7H-5,10-diaza-benzo[c]fluoren-6-yl ester (Reference Example 6c-1) and toluene-4-sulfonic acid 7-oxo-7H-5,9-diaza-benzo[c]fluoren-6-yl ester (Reference Example 6c-2) were obtained as yellow powders starting from the compound of Reference Example 6b.

Toluene-4-sulfonic acid 7-oxo-7H-5,10-diaza-benzo[c]fluoren-6-yl ester (Reference Example 6c-1):

ESI-MS: m/z 403 (MH$^+$); $^1$H-NMR (CDCl$_3$): δ 2.49 (3H, s), 7.42 (2H, d=7.9 Hz), 7.68 (1H, dd, J=1.0 Hz, 4.6 Hz), 7.72–7.81 (1H, m), 7.88–7.96 (1H, m), 8.04 (1H, d, J=8.6 Hz), 8.14 (2H, d, J=7.9 Hz), 8.46 (1H, d, J=8.3 Hz), 9.49 (1H, s).

Toluene-4-sulfonic acid 7-oxo-7H-5,9-diaza-benzo[c]fluoren-6-yl ester (Reference Example 6c-2):

ESI-MS: m/z 403 (MH$^+$); $^1$H-NMR (CDCl$_3$): δ 2.49 (3H, s), 7.43 (2H, d, 8.4 Hz), 7.76 (1H, ddd, J=1.4 Hz, 7.0 Hz, 8.6 Hz), 7.92 (1H, ddd, J=1.4 Hz, 7.0 Hz, 8.1 Hz), 8.04–8.09 (2H, m), 8.14 (2H, d, J=8.4 Hz), 8.46 (1H, dd, J=8.6 Hz, 1.4 Hz), 8.96 (1H, d, J=4.9 Hz), 9.01 (1H, d, J=0.5 Hz).

Reference Example 7

Preparation of toluene-4-sulfonic acid 3-chloro-7-oxo-7H-5,10-diaza-benzo[c]fluoren-6-yl ester (Reference Example 7c-1) and toluene-4-sulfonic acid 3-chloro-7-oxo-7H-5,9-diaza-benzo[c]fluoren-6-yl ester (Reference Example 7c-2)

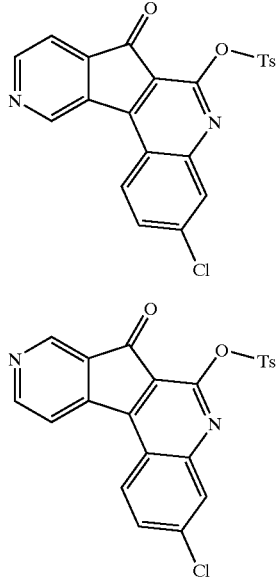

a) Preparation of 5,7-dioxo-6,7-dihydro-5H-[2]pyrindine-6-carboxylic acid (3-chloro-phenyl)-amide In a similar manner to Reference Example 1a, 5,7-dioxo-6,7-dihydro-5H-[2]pyrindine-6-carboxylic acid (3-chloro-phenyl)-amide was obtained starting from 5,7-dioxo-6,7-dihydro-5H-[2]pyrindine-6-carboxylic acid ethyl ester and 3-chloro-phenylamine. The desired product was obtained as a brownish orange powder.

ESI-MS: m/z 301 (MH$^+$); $^1$H-NMR (DMSO-d$_6$): δ 6.96–7.00 (1H, m), 7.27–7.29 (2H, m), 7.35 (1H, dd, J=1.3 Hz, 4.6 Hz), 7.98–7.99 (1H, m), 8.53 (1H, d, J=10.0 Hz), 8.74 (1H, d, J=4.6 Hz), 10.92 (1H, brs).

b) Preparation of a mixture of 3-chloro-5H-5,9-diaza-benzo[c]fluorene-6,7-dione and 3-chloro-5H-5,10-diaza-benzo[c]fluorene-6,7-dione In a similar manner to Reference Example 6b, a mixture of 3-chloro-5H-5,9-diaza-benzo[c]fluorene-6,7-dione and 3-chloro-5H-5,10-diaza-benzo[c]fluorene-6,7-dione was obtained starting from the compound of Reference Example 7a as a dark brown solid.

ESI-MS: m/z 283 (MH$^+$).

c) Preparation of toluene-4-sulfonic acid 3-chloro-7-oxo-7H-5,10-diaza-benzo[c]fluoren-6-yl ester (Reference Example 7c-1) and toluene-4-sulfonic acid 3-chloro-7-oxo-7H-5,9-diaza-benzo[c]fluoren-6-yl ester (Reference Example 7c-2)

In a similar manner to Reference Example 2c, toluene-4-sulfonic acid 3-chloro-7-oxo-7H-5,10-diaza-benzo[c]fluoren-6-yl ester (Reference Example 7c-1) and toluene-4-sulfonic acid 3-chloro-7-oxo-7H-5,9-diaza-benzo[c]fluoren-6-yl ester (Reference Example 7c-2) were obtained as yellow powders starting from the compound of Reference Example 7b.

Toluene-4-sulfonic acid 3-chloro-7-oxo-7H-5,10-diaza-benzo[c]fluoren-6-yl ester (Reference Example 7c-1):

ESI-MS: m/z 437 (M$^+$), 439 (MH$_2^+$); $^1$H-NMR (CDCl$_3$): δ 2.50 (3H, s), 7.43 (2H, d=8.1 Hz), 7.67–7.74 (2H, m), 8.01 (1H, d, J=1.9 Hz), 8.13 (2H, d, J=8.1 Hz), 8.39 (1H, d, J=8.9 Hz), 8.94 (1H, d, J=4.3 Hz), 9.43 (1H, s).

Toluene-4-sulfonic acid 3-chloro-7-oxo-7H-5,9-diaza-benzo[c]fluoren-6-yl ester (Reference Example 7c-2):

ESI-MS: m/z 437 (MH$^+$); $^1$H-NMR (CDCl$_3$): δ 2.50 (3H, s), 7.44 (2H, d, 8.1 Hz), 7.68 (1H, dd, J=2.4 Hz, 9.2 Hz), 7.97–8.00 (2H, m), 8.13 (2H, d, J=8.1 Hz), 8.35 (1H, d, J=9.2 Hz), 8.96 (1H, d, J=4.9 Hz), 8.99 (1H, s).

Example 1

Preparation of 3-methoxy-6-(2-{methyl-[2-(3-methoxy-7-oxo-7H-5,9-diaza-benzo[c]fluoren-6-ylamino)-ethyl]-amino}-ethylamino)-5,9-diaza-benzo[c]fluoren-7-one

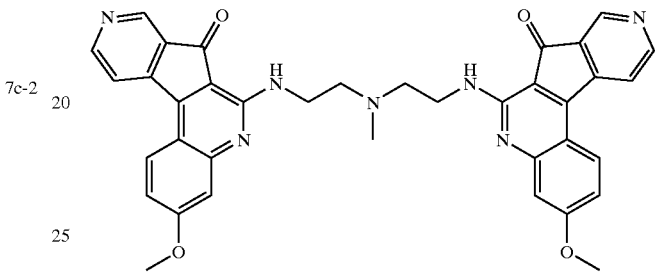

A mixture of 6-chloro-3-methoxy-5,9-diaza-benzo[c]fluoren-7-one (Reference Example 1c-2) (21 mg) and N-methyl-2,2'-diaminodiethylamine (WAKO PURE CHEMICAL: 3.3 mg) and potassium carbonate (10 mg) was suspended in N,N-dimethylformamide (0.5 ml) and stirred at 90° C. for thirteen hours under nitrogen gas. The mixture was evaporated to dryness. The residue was purified by silica gel column chromatography developed by dichloromethane-methanol=30:1 and dichloromethane-methanol-ammonia water (25%)=30:1:0.4. The desired product was obtained as a reddish powder.

ESI-MS: m/z 638 (MH$^+$); $^1$H-NMR (CDCl$_3$): δ 2.57 (3H, s), 2.88 (4H, brt, J=ca 6 Hz), 3.69 (4H, q-like, J=ca 6 Hz), 3.87 (6H, s), 6.78 (2H, dd, J=9.2 Hz, 2.7 Hz), 6.85 (2H, d, J=2.7 Hz), 7.19 (2H, brt, J=ca 5 Hz), 7.50 (2H, dd, J=4.9 Hz, 1 Hz), 7.66 (2H, d, J=9.2 Hz), 8.41 (2H, d, 1 Hz), 8.69 (2H, d, J=4.9 Hz).

Example 2

Preparation of 3-methoxy-6-{2-[methyl-(2-{methyl-[2-(3-methoxy-7-oxo-7H-5,9-diaza-benzo[c]fluoren-6-ylamino)-ethyl]-amino}-ethyl)-amino]-ethylamino}-5,9-diaza-benzo[c]fluoren-7-one

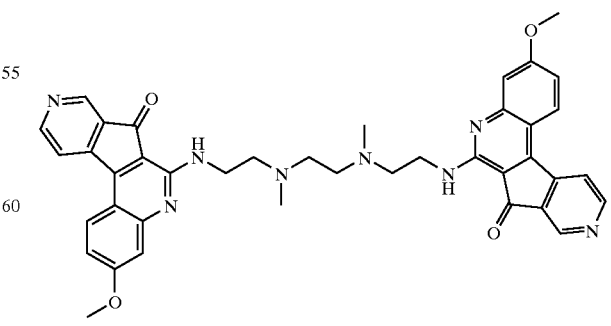

In a similar manner to Example 1, 3-methoxy-6-{2-[methyl-(2-{methyl-[2-(3-methoxy-7-oxo-7H-5,9-diazabenzo[c]fluoren-6-ylamino)-ethyl]-amino}-ethyl)-amino]-ethylamino}-5,9-diaza-benzo[c]fluoren-7-one was obtained starting from the compound of Reference Example 1c-2 and N1-{2-[(2-amino-ethyl)-methyl-amino]-ethyl}-N-1-methyl-ethane-1,2-diamine (Swarna A. Gamage et al., J. Med. Chem., Vol. 44, pp. 1407–1415, 2001). The desired product was obtained as a reddish powder.

ESI-MS: m/z 695 (MH$^+$); $^1$H-NMR (CDCl$_3$): δ 2.39 (6H, s), 2.80 (4H, s), 2.93 (4H, brt, J=ca 6 Hz), 3.59 (4H, q-like, J=ca 6 Hz), 3.77 (6H, s), 6.25 (2H, d, J=2.7 Hz), 3.77 (2H, dd, J=2.4 Hz, 8.9 Hz), 7.11 (2H, dd, J=5.1 Hz, 1 Hz), 7.48 (2H, d, J=9.2 Hz), 7.55 (2H, brt, J=ca 5 Hz), 8.51 (2H, d, J=6.2 Hz), 8.75 (2H, d, 1 Hz).

Example 3

Preparation of 3-methoxy-6-{2-[(3-{[2-(3-methoxy-7-oxo-7H-5,9-diaza-benzo[c]fluoren-6-ylamino)-ethyl]-methyl-amino}-propyl)-methyl-amino]-ethylamino}-5,9-diaza-benzo[c]fluoren-7-one In a similar manner to Example 1, 3-methoxy-6-{2-[(3-{[2-(3-methoxy-7-oxo-7H-5,9-diaza-benzo[c]fluoren-6-ylamino)-ethyl]-methyl-amino}-propyl)-methyl-amino]-ethylamino}-5,9-diaza-benzo[c]fluoren-7-one was obtained starting from the compound of Reference Example 1c-2 and N,N'-bis-(2-amino-ethyl)-N,N'-dimethyl-propane-1,3-diamine (Swarna A. Gamage et al., J. Med. Chem., Vol. 44, pp. 1407–1415, 2001). The desired product was obtained as a reddish powder.

ESI-MS: m/z 709 (MH$^+$); $^1$H-NMR (CDCl$_3$): δ 1.83–1.95 (2H, m), 2.30 (6H, s), 2.68–2.84 (8H, m), 3.63–3.68 (4H, m), 3.84 (6H, s), 6.47 (2H, d, J=2.4 Hz), 6.78 (2H, dd, J=2.5 Hz, 9.6 Hz), 7.21 (2H, d, J=4.8 Hz), 7.46 (2H, brt, J=ca 5 Hz), 7.52 (2H, d, J=8.8 Hz), 8.54 (1H, d, J=4.8 Hz), 8.71 (1H, s).

Example 4

Preparation of 6-(3-{methyl-[3-(7-oxo-7H-5,9-diaza-benzo[c]fluoren-6-ylamino)-propyl]-amino}-propylamino)-5,9-diaza-benzo[c]fluoren-7-one

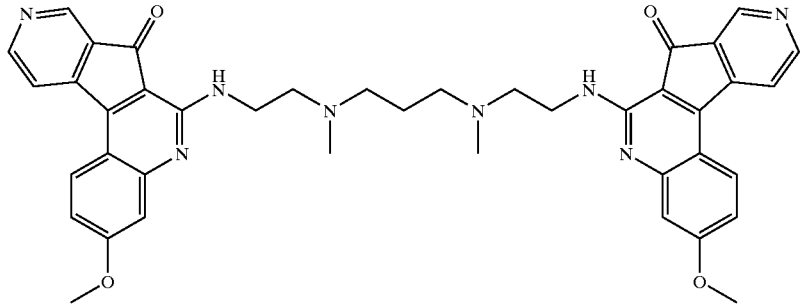

A mixture of toluene-4-sulfonic acid 7-oxo-7H-5,9-diaza-benzo[c]fluoren-6-yl ester (Reference Example 6c-2) (90 mg) and N$^1$-(3-amino-propyl)-N$^1$-methyl-propane-1,3-diamine (WAKO PURE CHEMICAL: 15 mg) and potassium carbonate (37 mg) was suspended in dichloromethane (10 ml) and heated at reflux temperature for five days under nitrogen. The mixture was roughly purified by short silica gel column chromatography developed by dichloromethane-methanol=100:1 and dichloromethane-methanol=1:1. The fractions that contained the desired product were combined and evaporated to dryness and purified again by silica gel thin layer chromatography developed by dichloromethane-methanol-ammonia water=90:10:1. The desired compound was obtained as a dark reddish powder.

ESI-MS: m/z 606 (MH$^+$); $^1$H-NMR (CDCl$_3$): δ 1.92–2.02 (4H, m), 2.44 (3H, s), 2.67 (4H, t, J=6.5 Hz), 3.74 (4H, q-like, J=ca 6 Hz), 7.12–7.20 (2H, m), 7.32–7.45 (6H, m), 7.56 (2H, dd, J=1.1 Hz, 5.1 Hz), 7.84 (2H, d, J=8.1 Hz), 8.67 (2H, d, J=4.9 Hz), 8.72 (2H, d, J=1.1 Hz).

Example 5

Preparation of 6-{2-[methyl-(3-{methyl-[2-(7-oxo-7H-5,9-diaza-benzo[c]fluoren-6-ylamino)-ethyl]-amino}-propyl)-amino]-ethylamino}-5,9-diaza-benzo[c]fluoren-7-one

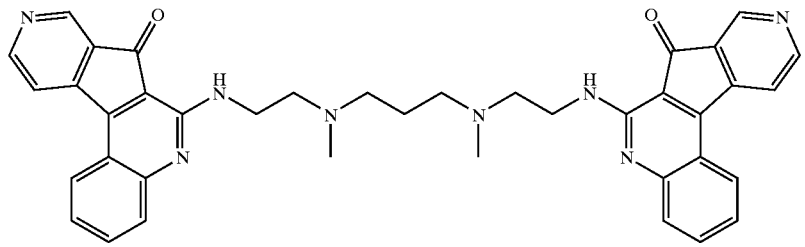

In a similar manner to Example 4, 6-{2-[methyl-(3-{methyl-[2-(7-oxo-7H-5,9-diaza-benzo[c]fluoren-6-ylamino)-ethyl]-amino}-propyl)-amino]-ethylamino}-5,9-diaza-benzo[c]fluoren-7-one was obtained starting from the compound of Reference Example 6c-2 and N,N'-bis-(2-amino-ethyl)-N,N'-dimethyl-propane-1,3-diamine. The desired product was obtained as a reddish powder.

ESI-MS: m/z 649 (MH$^+$); $^1$H-NMR (CDCl$_3$): δ 1.82–1.96 (2H, m), 2.30 (6H, s), 2.72 (4H, brt, J=ca 6 Hz), 2.79 (4H, brt, J=ca 6 Hz), 3.60–3.70 (2H, m), 7.10–7.17 (2H, m), 7.28–7.47 (8H, m), 7.68 (2H, brd, J=ca 8 Hz), 8.56 (2H, d, J=4.9 Hz), 8.68 (2H, d, J=0.5 Hz).

Example 6

Preparation of 3-chloro-6-{2-[(3-{[2-(3-chloro-7-oxo-7H-5,9-diaza-benzo[c]fluoren-6-ylamino)-ethyl]-methyl-amino}-propyl)-methyl-amino]-ethylamino}-5,9-diaza-benzo[c]fluoren-7-one

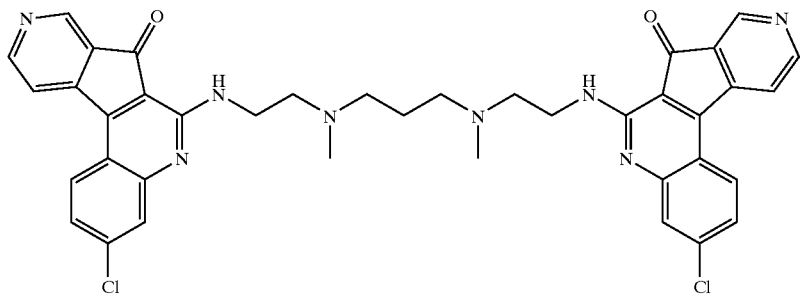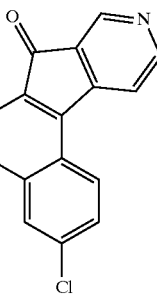

In a similar manner to Example 4, this compound was obtained starting from 3-chloro-6-(toluene-4-sulfonylmethyl)-5,9-diaza-benzo[c]fluoren-7-one (the compound of Reference Example 7c-2) and N,N'-bis-(2-amino-ethyl)-N,N'-dimethyl-propane-1,3-diamine. The desired product was obtained as a reddish powder.

ESI-MS: m/z 717 (MH$^+$); $^1$H-NMR (CDCl$_3$) δ: 1.92 (2H, t, J=6.5 Hz), 2.32 (6H, s), 2.78 (8H, quartet like, J=ca 5.5 Hz), 3.60 (4H, quartet like, J=ca 5.5 Hz), 7.07 (2H, dd, J=9.0 Hz, 2.0 Hz), 7.11 (2H, brs), 7.28 (2H, d, J=5.0 Hz), 7.51 (2H, brs), 7.53 (2H, d, J=9.0 Hz), 8.72 (2H, d, J=5.0 Hz), 8.76 (2H, s).

Example 7

Preparation of 6-(2-{4-[2-(7-oxo-7H-5,9-diaza-benzo[c]fluoren-6-ylamino)-ethyl]-piperazin-1-yl}-ethylamino)-5,9-diaza-benzo[c]fluoren-7-one

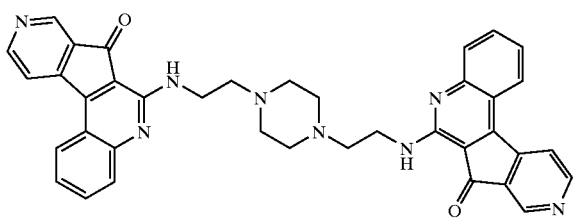

In a similar manner to Example 4, 6-(2-{4-[2-(7-oxo-7H-5,9-diaza-benzo[c]-fluoren-6-ylamino)-ethyl]-piperazin-1-yl}-ethylamino)-5,9-diaza-benzo[c]fluoren-7-one was obtained starting from the compound of Reference Example 6c-2 and 2-[4-(2-amino-ethyl)-piperazin-1-yl]-ethylamine (see, Swarna A. Gamage et al., J. Med. Chem., Vol. 44, pp. 1407–1415, 2001). The desired product was obtained as a reddish powder.

ESI-MS: m/z 633 (MH$^+$); $^1$H-NMR (CDCl$_3$): δ 2.62–2.94 (12H, m), 3.81–3.90 (4H, m), 7.28–7.48 (4H, m), 7.64–7.77 (4H, m), 7.96 (2H, d, J=4.3 Hz), 8.18 (2H, brd, J=8.3 Hz), 8.87 (2H, s), 8.90 (2H, d, J=5.3 Hz).

Example 8

Preparation of 6-(3-{4-[3-(7-oxo-7H-5,9-diaza-benzo[c]fluoren-6-ylamino)-propyl]-piperazin-1-yl}-propylamino)-5,9-diaza-benzo[c]fluoren-7-one

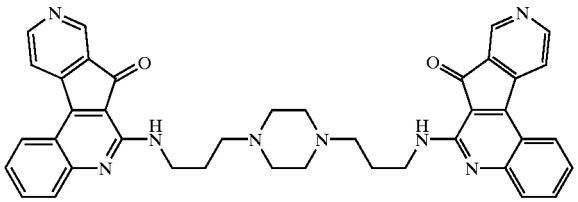

In a similar manner to Example 4, 6-(3-{4-[3-(7-oxo-7H-5,9-diaza-benzo[c]fluoren-6-ylamino)-propyl]-piperazin-1-yl}-propylamino)-5,9-diaza-benzo[c]fluoren-7-one was obtained starting from the compound of Reference Example 6c-2 and 3-[4-(3-amino-propyl)-piperazin-1-yl]-propylamine (Wako Pure Chemical). The desired product was obtained as a reddish powder.

ESI-MS: m/z 661 (MH$^+$); $^1$H-NMR (CDCl$_3$): δ 1.85–2.02 (4H, m), 2.40–2.80 (12H, m), 3.77 (4H, q-like, J=ca 7 Hz), 7.20 (2H, brt, J=ca 6 Hz), 7.29–7.35 (2H, m), 7.63–7.76 (4H, m), 7.93 (2H, dd, J=1 Hz, 5.0 Hz), 8.17 (2H, brd, J=ca 8 Hz), 8.86 (2H, d, J=4.9 Hz), 8.89 (2H, d, J=0.7 Hz).

Example 9

Preparation of 3-methoxy-6-{2-[(3-{[2-(3-methoxy-8-methyl-7-oxo-7H-5,9-diaza-benzo[c]fluoren-6-ylamino)-ethyl]-methyl-amino}-propyl)-methyl-amino]-ethylamino}-8-methyl-5,9-diaza-benzo[c]fluoren-7-one

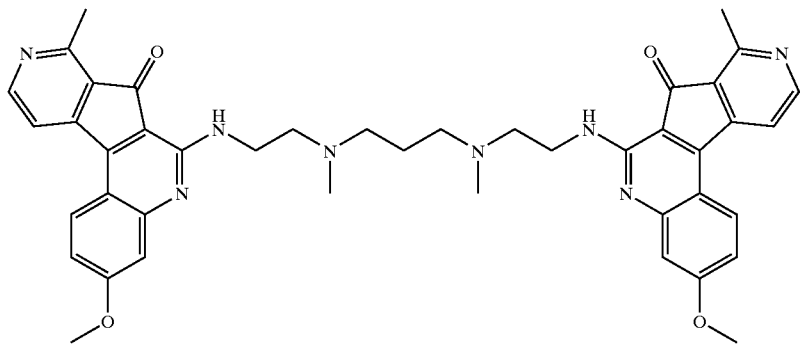

In a similar manner to Example 4,3-methoxy-6-{2-[(3-{[2-(3-methoxy-8-methyl-7-oxo-7H-5,9-diaza-benzo[c]fluoren-6-ylamino)-ethyl]-methyl-amino}-propyl)-methyl-amino]-ethylamino}-8-methyl-5,9-diaza-benzo[c]fluoren-7-one was obtained starting from the compound of Reference Example 4 and N,N'-bis-(2-amino-ethyl)-N,N'-dimethyl-propane-1,3-diamine. The desired product was obtained as a reddish powder.

ESI-MS: m/z 737 (MH$^+$); $^1$H-NMR (CDCl$_3$): δ 1.86–2.01 (4H, m), 2.30 (6H, s), 2.68–2.90 (14H, m), 3.58–3.70 (4H, m), 3.87 (6H, s), 6.50 (2H, d, J=2.6 Hz), 6.77 (2H, dd, J=2.6 Hz, 8.9 Hz), 7.01 (2H, d, J=5.0 Hz), 7.47–7.57 (4H, m), 8.36 (2H, d, J=5.0 Hz).

Example 10

Preparation of 6-{2-[methyl-(3-{methyl-[2-(7-oxo-7H-5,10-diaza-benzo[c]fluoren-6-ylamino)-ethyl]-amino}-propyl)-amino]-ethylamino}-5,10-diaza-benzo[c]fluoren-7-one

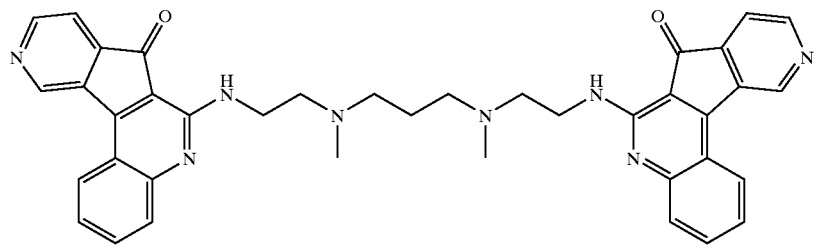

In a similar manner to Example 4, this compound was obtained starting from toluene-4-sulfonic acid 7-oxo-7H-5,10-diaza-benzo[c]fluoren-6-yl ester (the compound of Reference Example 6c-1) and N,N'-bis-(2-amino-ethyl)-N,N'-dimethyl-propane-1,3-diamine. The desired product was obtained as a reddish powder.

ESI-MS: m/z 649 (MH$^+$); $^1$H-NMR (CDCl$_3$) δ: 1.91 (2H, t, J=6.5 Hz), 2.32 (6H, s), 2.75 (4H, t, J=6.5 Hz), 2.80 (4H, t, J=6.0 Hz), 3.65 (4H, q, J=5.5 Hz), 7.14–7.23 (4H, m), 7.32 (2H, dd, J=4.5 Hz, 1.0 Hz), 7.38–7.48 (4H, m), 7.64 (2H, d, J=7.5 Hz), 8.62 (2H, d, J=4.5 Hz), 8.71 (2H, s).

Example 11

Preparation of 3-methoxy-6-{2-[(3-{[2-(3-methoxy-4-methyl-7-oxo-7H-5,10-diaza-benzo[c]fluoren-6-ylamino)-ethyl]-methyl-amino}-propyl)-methyl-amino]-ethylamino}-4-methyl-5,10-diaza-benzo[c]fluoren-7-one

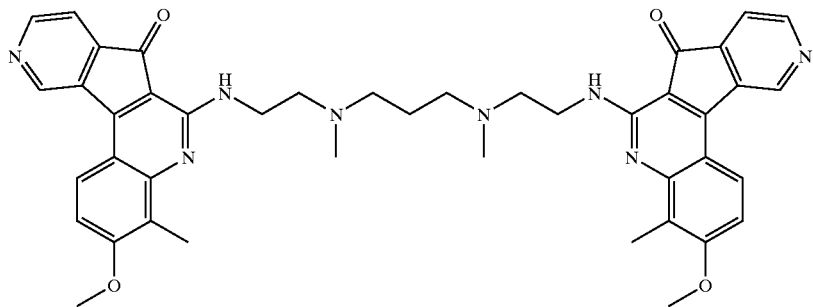

In a similar manner to Example 4, 3-methoxy-6-{2-[(3-{[2-(3-methoxy-4-methyl-7-oxo-7H-5,10-diaza-benzo[c]fluoren-6-ylamino)-ethyl]-methyl-amino}-propyl)-methyl-amino]-ethylamino}-4-methyl-5,10-diaza-benzo[c]fluoren-7-one was obtained starting from toluene-4-sulfonic acid 3-methoxy-4-methyl-7-oxo-7H-5,10-diaza-benzo[c]fluoren-6-yl ester (the compound of Reference Example 2c-1) and N,N'-bis-(2-amino-ethyl)-N,N'-dimethyl-propane-1,3-diamine. The desired product was obtained as a reddish powder.

ESI-MS: m/z 737 (MH$^+$); $^1$H-NMR (CDCl$_3$): δ 1.91 (2H, t, J=6.5 Hz), 2.19 (6H, s), 2.36 (6H, s), 2.80–2.87 (8H, m), 3.71 (4H, quartet like, J=ca 5.5 Hz), 3.96 (6H, s), 6.90 (2H, d, J=9 Hz), 7.22 (2H, brt, J=ca 4.5 Hz), 7.26 (2H, d, J=4.5 Hz), 7.58 (2H, d, J=9 Hz), 8.57 (2H, d, J=9 Hz), 8.69 (2H, s).

Example 12

Preparation of 3-chloro-6-{2-[(3-{[2-(3-chloro-7-oxo-7H-5,10-diaza-benzo[c]fluoren-6-ylamino)-ethyl]-methyl-amino}-propyl)-methyl-amino]-ethylamino}-5,10-diaza-benzo[c]fluoren-7-one

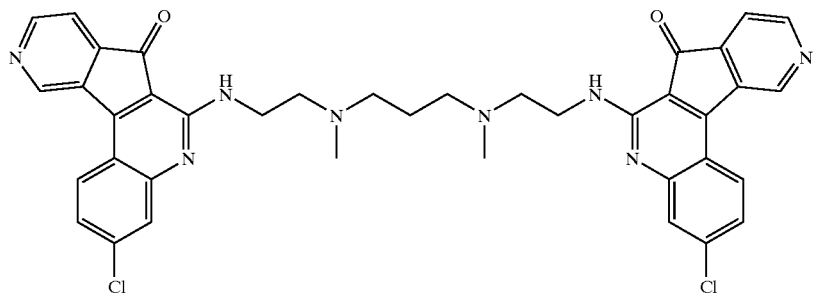

In a similar manner to Example 4, this compound was obtained starting from toluene-4-sulfonic acid 3-chloro-7-oxo-7H-5,10-diaza-benzo[c]fluoren-6-yl ester (the compound of Reference Example 7c-1) and N,N'-bis-(2-amino-ethyl)-N,N'-dimethyl-propane-1,3-diamine. The desired product was obtained as a reddish powder.

ESI-MS: m/z 717 (MH$^+$); $^1$H-NMR (CDCl$_3$) δ: 1.93 (2H, t, J=6.5 Hz), 2.34 (6H, s), 2.78 (4H, t, J=6.5 Hz), 2.81 (4H, t, J=5.5 Hz), 3.64 (4H, q, J=5.5 Hz), 7.10 (2H, dd, J=9.0 Hz, 2.0 Hz), 7.21 (2H, d, J=2.0 Hz), 7.36 (2H, dd, J=4.5 Hz, 1.0 Hz), 7.42 (2H, brt, J=ca 5.0 Hz), 7.58 (2H, d, J=9.0 Hz), 8.71 (2H, d, J=4.5 Hz), 8.78 (2H, s).

Example 13

Preparation of 11-chloro-6-{2-[(3-{[2-(11-chloro-3-methoxy-4-methyl-7-oxo-7H-5,10-diaza-benzo[c]fluoren-6-ylamino)-ethyl]-methyl-amino}-propyl)-methylamino]-ethylamino}-3-methoxy-4-methyl-5,10-diaza-benzo[c]fluoren-7-one

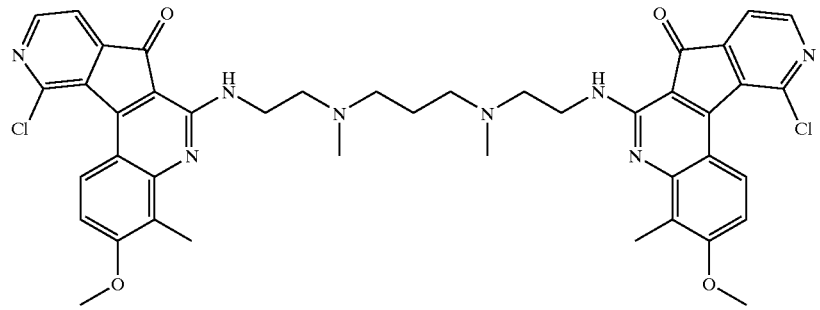

In a similar manner to Example 4, this compound was obtained starting from toluene-4-sulfonic acid 11-chloro-3-methoxy-4-methyl-7-oxo-7H-5,10-diaza-benzo[c]fluoren-6-yl ester (the compound of Reference Example 5) and N,N'-bis-(2-amino-ethyl)-N,N'-dimethyl-propane-1,3-diamine. The desired product was obtained as a reddish powder.

ESI-MS: m/z 805 (MH$^+$); $^1$H-NMR (CDCl$_3$) δ: 1.87 (2H, t, J=6.5 Hz), 2.23 (6H, s), 2.31 (6H, s), 2.74 (4H, t, J=6.5 Hz), 2.81 (4H, t, J=5.5 Hz), 3.70 (4H, quartet like, J=ca 5.5 Hz), 3.98 (6H, s), 6.93 (2H, d, J=9.6 Hz), 7.24 (2H, d, J=4.3 Hz), 7.46 (2H, brt, J=ca 5.5 Hz), 8.36 (2H, d, J=4.3 Hz), 8.72 (2H, d, J=9.6 Hz).

Example 14

Preparation of 3-methoxy-6-{2-[(3-{[2-(3-methoxy-9-methyl-7-oxo-7H-5,10-diaza-benzo[c]fluoren-6-ylamino)-ethyl]-methyl-amino}-propyl)-methyl-amino]-ethylamino}-9-methyl-5,10-diaza-benzo[c]fluoren-7-one

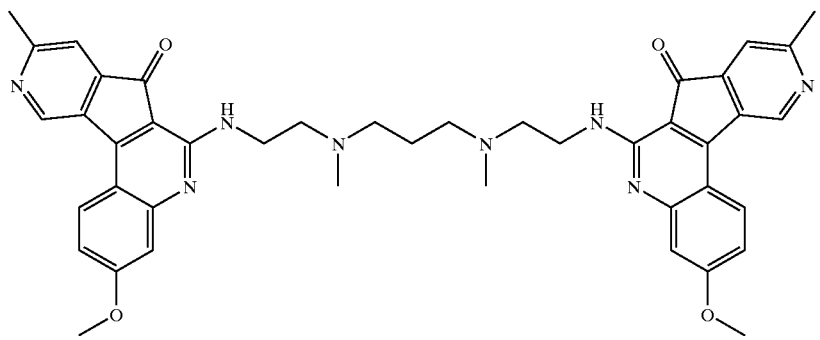

In a similar manner to Example 4, 3-methoxy-6-{2-[(3-{[2-(3-methoxy-9-methyl-7-oxo-7H-5,10-diaza-benzo[c]fluoren-6-ylamino)-ethyl]-methyl-amino}-propyl)-methyl-amino]-ethylamino}-9-methyl-5,10-diaza-benzo[c]fluoren-7-one was obtained starting from the compound of Reference Example 3 and N,N'-bis-(2-amino-ethyl)-N,N'-dimethyl-propane-1,3-diamine. The desired product was obtained as a reddish powder.

ESI-MS: m/z 737 (MH$^+$); $^1$H-NMR (CDCl$_3$): δ 1.82–1.95 (4H, m), 2.30 (6H, s), 2.56 (6H, s), 2.65–2.82 (8H, m), 3.58–3.68 (4H, m), 3.86 (6H, s), 6.58 (2H, d, J=2.6 Hz), 6.81 (2H, dd, J=2.6 Hz, 9.2 Hz), 7.14 (2H, s), 7.42 (2H, brt, J=ca 5 Hz), 7.52 (2H, d, J=9.2 Hz), 8.58 (2H, s).

Example 15

Preparation of 6-{2-[methyl-(3-{methyl-[2-(7-oxo-7H-5,10-diaza-benzo[c]fluoren-6-ylamino)-ethyl]-amino}-propyl)-amino]-ethylamino}-5,9-diaza-benzo[c]fluoren-7-one

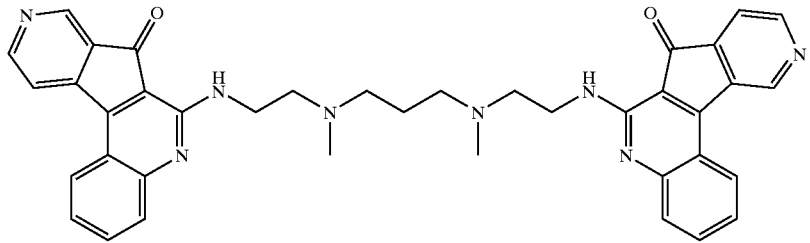

a) Preparation of 6-[2-({3-[(2-amino-ethyl)-methyl-amino]-propyl}-methyl-amino)-ethylamino]-5,9-diaza-benzo[c]fluoren-7-one A mixture of toluene-4-sulfonic acid 7-oxo-7H-5,9-diaza-benzo[c]fluoren-6-yl ester (102 mg) (the compound of Reference Example 6c-2) and N,N'-bis-(2-amino-ethyl)-N,N'-dimethyl-propane-1,3-diamine (0.8 ml) was stirred at 50° C. for 20 minutes. The reaction mixture was diluted with dichloromethane. The solution was washed with saturated NaHCO$_3$ solution and dried over magnesium sulfate. The organic layer was evaporated to dryness. The residue was purified by silica gel column chromatography developed by dichloromethane-methanol-ammonia water (25%)=90:10:1. The desired product (37 mg) was obtained as a reddish oil.

ESI-MS: m/z 419 (MH$^+$); $^1$H-NMR (CDCl$_3$) δ: 1.72 (2H, quintet, J=:6 Hz), 2.22 (3H, s), 2.34 (3H, s), 2.39–2.50 (6H, m), 2.70–2.78 (4H, m), 3.77 (2H, q, J=6 Hz), 7.31–7.36 (1H, m), 7.65–7.77 (2H, m), 7.95 (1H, d, J=5.0 Hz), 8.18 (1H, d, J=8.0 Hz), 8.87 (1H, d, J=5.0 Hz), 8.88 (1H, s).

b) Preparation of 6-{2-[methyl-(3-{methyl-[2-(7-oxo-7H-5,10-diaza-benzo[c]fluoren-6-ylamino)-ethyl]-amino}-propyl)-amino]-ethylamino}-5,9-diaza-benzo[c]fluoren-7-one To a solution of 6-[2-({3-[(2-amino-ethyl)-methyl-amino]-propyl}-methyl-amino)-ethylamino]-5,9-diaza-benzo[c]fluoren-7-one (10.3 mg) obtained above in dichloromethane (0.8 ml) were added K$_2$CO$_3$ (6.2 mg) and toluene-4-sulfonic acid 7-oxo-7H-5,10-diaza-benzo[c]fluoren-6-yl ester (19.6 mg) (the compound of Reference Example 6c-1). The mixture was stirred at 40° C. for 2 days. The solution was cooled to room temperature and the solvent was removed under reduced pressure. The residue was purified by preparative TLC developed by dichloromethane-methanol-ammonia water (25%)=180:20:1. The desired product (6.9 mg) was obtained as a reddish powder.

ESI-MS: m/z 649 (MH$^+$); $^1$H-NMR (CDCl$_3$) δ: 1.88 (2H, t, J=6.5 Hz), 2.29 (3H, s), 2.30 (3H, s), 2.72 (4H, t, J=6.5 Hz), 2.78 (4H, t, J=6.0 Hz), 3.64 (4H, quartet like, J=ca 6 Hz), 7.10–7.47 (8H, m), 7.62–7.68 (2H, m), 8.54 (1H, d, J=5.0 Hz), 8.64 (1H, d, J=4.5 Hz), 8.67 (1H, s), 8.72 (1H, s).

Example 16

Preparation of 3-methoxy-6-{2-[methyl-(3-{methyl-[2-(7-oxo-7H-5,9-diaza-benzo[c]fluoren-6-ylamino)-ethyl]-amino}-propyl)-amino]-ethylamino}-5,9-diaza-benzo[c]fluoren-7-one

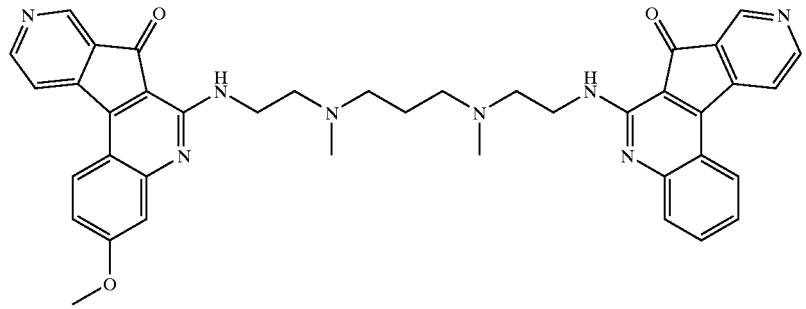

a) Preparation of 6-[2-({3-[(2-amino-ethyl)-methyl-amino]-propyl}-methyl-amino)-ethylamino]-3-methoxy-5,9-diaza-benzo[c]fluoren-7-one A mixture of 6-chloro-3-methoxy-5,9-diaza-benzo[c]fluoren-7-one (50.8 mg) (the compound of Reference Example 1c-2) and N,N'-bis-(2-amino-ethyl)-N,N'-dimethyl-propane-1,3-diamine (0.5 ml) was stirred at 50° C. for 4 hours. The reaction mixture was diluted with dichloromethane. The solution was washed with saturated NaHCO$_3$ solution and dried over magnesium sulfate. The organic layer was evaporated to dryness. The residue was purified by silica gel column chromatography developed by dichloromethane-methanol-ammonia water (25%)=90:10:1. The desired product (49 mg) was obtained as a reddish oil.

ESI-MS: m/z 449 (MH⁺); ¹H-NMR (CDCl₃) δ: 1.72 (2H, quintet, J=7.0 Hz), 2.28 (3H, s), 2.33 (3H, s), 2.40–2.53 (6H, m), 2.69 (2H, t, J=6.0 Hz), 2.76 (2H, t, J=6.5 Hz), 3.48 (2H, s), 3.75 (2H, quartet like, J=ca 6 Hz), 3.97 (3H, s), 6.97 (1H, dd, J=9.0 Hz, 2.5 Hz), 7.09 (1H, d, J=2.5 Hz), 7.42 (1H, brt, J=ca 5 Hz), 7.87 (1H, dd, J=5.0 Hz, 1.0 Hz), 8.05 (1H, d, J=9.0 Hz), 8.83 (1H, d, J=5.0 Hz), 8.85 (1H, d, J=1.0 Hz).

b) Preparation of 3-methoxy-6-{2-[methyl-(3-{methyl-[2-(7-oxo-7H-5,9-diaza-benzo[c]fluoren-6-ylamino)-ethyl]-amino}-propyl)-amino]-ethylamino}-5,9-diaza-benzo[c]fluoren-7-one To a solution of 6-[2-({3-[(2-amino-ethyl)-methyl-amino]-propyl}-methyl-amino)-ethylamino]-3-methoxy-5,9-diaza-benzo[c]fluoren-7-one (12.0 mg) obtained above in dichloromethane (1 ml) were added K₂CO₃ (9.4 mg) and toluene-4-sulfonic acid 7-oxo-7H-5,9-diaza-benzo[c]fluoren-6-yl ester (17.2 mg) (the compound of Reference Example 6c-2). The mixture was stirred at 40° C. for 1 day. The solution was cooled to room temperature and the solvent was removed under reduced pressure. The residue was purified by preparative TLC developed by dichloromethane-methanol-ammonia water (25%)= 180:20:1. The desired product (4.4 mg) was obtained as a reddish powder.

ESI-MS: m/z 679 (MH⁺); ¹H-NMR (CDCl₃) δ: 1.92 (2H, t, J=6.5 Hz), 2.30 (3H, s), 2.35 (3H, s), 2.73–2.86 (8H, m), 3.60–3.73 (4H, m), 3.83 (3H, s), 6.54 (1H, d, J=2.5 Hz), 6.75 (1H, dd, J=9.0 Hz, 2.5 Hz), 7.14–7.49 (5H, m), 7.73 (2H, d, J=9.0 Hz), 8.52 (1H, d, J=5.0 Hz), 8.58 (1H, d, J=5.0 Hz), 8.69 (2H, d, J=5.0 Hz).

Example 17

Preparation of 3-hydroxy-6-{2-[(3-{[2-(3-hydroxy-7-oxo-7H-5,9-diaza-benzo[c]fluoren-6-ylamino)-ethyl]-methyl-amino}-propyl)-methyl-amino]-ethylamino}-5,9-diaza-benzo[c]fluoren-7-one

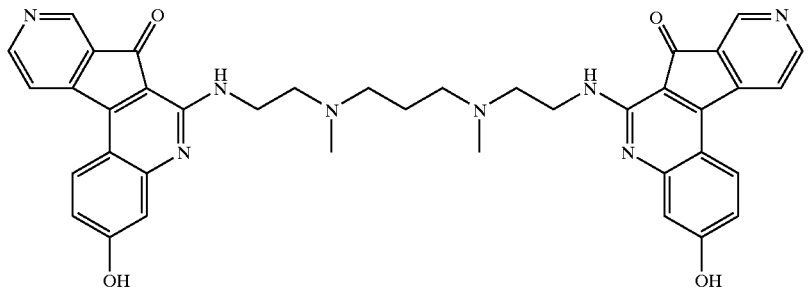

To a mixture of acetic acid (0.6 ml) and hydrobromic acid (48%, 0.6 ml) was added the compound of Example 3 (5.0 mg). The mixture was heated at 120° C. for nineteen hours. The mixture was cooled to room temperature and evaporated to dryness. The residue was purified by amino silica gel column chromatography developed by a mixture of dichloromethane-methanol=1:1 to give the desired compound. The desired product was obtained as a dark red powder.

ESI-MS: m/z 681 (MH⁺); ¹H-NMR (DMSO-d₆): δ 1.65–1.85 (4H, m), 2.20 (6H, s), 2.56–2.70 (8H, m), 3.45–3.56 (4H, m), 6.39 (2H, d, J=2.3 Hz), 6.75 (2H, dd, J=2.3 Hz, 8.9 Hz), 7.23 (2H, brt, J=ca 5.0 Hz), 7.65 (2H, d, J=4.9 Hz), 7.79 (2H, d, J=9.2 Hz), 8.52 (2H, s), 8.57 (2H, d, J=4.9 Hz).

Example 18

Preparation of 6-(3-{[3-(7-methoxyimino-7H-5,9-diaza-benzo[c]fluoren-6-ylamino)-propyl]-methyl-amino}-propylamino)-5,9-diaza-benzo[c]fluoren-7-one O-methyl-oxime

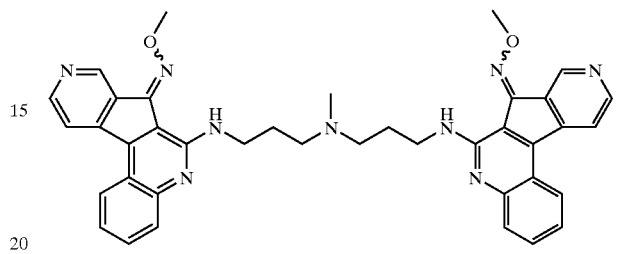

6-(3-{Methyl-[3-(7-oxo-7H-5,9-diaza-benzo[c]fluoren-6-ylamino)-propyl]-amino}-propylamino)-5,9-diaza-benzo[c]fluoren-7-one (the compound of Example 4, 10.1 mg) and O-methyl hydroxylammonium hydrochloride (18.1 mg) (Tokyo Kasei Ltd.) were dissolved in pyridine (1 ml) and the solution was stirred at 80° C. for 3.5 hours. The reaction mixture was diluted with dichloromethane and filtered through a glass filter. The solid obtained was dissolved in methanol and passed through a Mega Bond Elut SCX (Varian). The column was washed with methanol and the product was eluted with ammonia water (25%)-methanol= 1:20. The eluate was evaporated to dryness. The desired product was obtained as an orange powder.

ESI-MS: m/z 664 (MH⁺); ¹H-NMR (CDCl₃) δ: 2.04 (4H, quintet, J=6.5 Hz), 2.47 (3H, s), 2.77 (4H, t, J=6.5 Hz), 3.78 (4H, t, J=6.5 Hz), 4.26 (6H, s), 6.82 (2H, brt, J=ca 5.5 Hz), 7.19 (2H, t, J=8.5 Hz), 7.48 (2H, t, J=8.5 Hz), 7.66 (2H, d, J=8.5 Hz), 7.84 (2H, d, J=4.5 Hz), 8.02 (2H, d, J=8.5 Hz), 8.66 (2H, d, J=4.5 Hz), 9.26 (2H, s).

Example A

Hard gelatin capsules each containing the following ingredients were manufactured in a manner known in the art:

| | |
|---|---|
| 6-{2-[methyl-(3-{methyl-[2-(7-oxo-7H-5,9-diaza-benzo[c]fluoren-6-ylamino)-ethyl]-amino}-propyl)-amino]-ethylamino}-5,9-diaza-benzo[c]fluoren-7-one | 100 mg |
| Lactose | 56 mg |

-continued

| | |
|---|---|
| Crystalline Cellulose | 30 mg |
| Silicic acid, Light Anhydrous | 10 mg |
| Talc | 3 mg |
| Magnesium stearate | 1 mg |
| Total | 200 mg |

Example B

Tablets each containing the following ingredients were manufactured in a manner known in the art:

| | |
|---|---|
| 6-{2-[methyl-(3-{methyl-[2-(7-oxo-7H-5,9-diaza-benzo[c]fluoren-6-ylamino)-ethyl]-amino}-propyl)-amino]-ethylamino}-5,9-diaza-benzo[c]fluoren-7-one | 100 mg |
| Lactose | 60 mg |
| Corn starch | 20 mg |
| Sodium Starch Glycolate | 10 mg |
| Polyvinylpyrrolidone | 6 mg |
| Talc | 3 mg |
| Magnesium stearate | 1 mg |
| Total | 200 mg |

Example C

Injection solution/emulsion of each containing the following ingredients were manufactured in a manner known in the art:

| | |
|---|---|
| 6-{2-[methyl-(3-{methyl-[2-(7-oxo-7H-5,9-diaza-benzo[c]fluoren-6-ylamino)-ethyl]-amino}-propyl)-amino]-ethylamino}-5,9-diaza-benzo[c]fluoren-7-one | 50 mg |
| PEG400 | 50–250 mg |
| Lecithin | 100–250 mg |
| Soy oil | 7.5 mg |
| Glycerol | 40–60 mg |
| Water q.s. | 5 ml |

What is claimed is:

1. A polycyclic compound of formula [I],

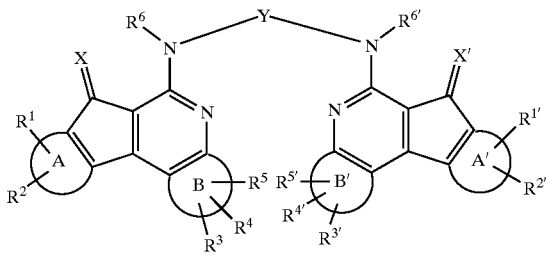

[I]

wherein
ring A is an unsubstituted nitrogen-containing 5 or 6 membered heteroaromatic ring or a substituted nitrogen-containing 5 or 6 membered heteroaromatic ring substituted by one or two groups independently selected from $R^1$ and $R^2$;

ring A' is an unsubstituted nitrogen-containing 5 or 6 membered heteroaromatic ring or a substituted nitrogen-containing 5 or 6 membered heteroaromatic ring substituted by one or two groups independently selected from $R^{1'}$ and $R^{2'}$;

ring B is an unsubstituted benzene ring, or a substituted benzene ring substituted by 1 to 3 groups independently selected from $R^3$, $R^4$ and $R^5$, an unsubstituted naphthalene ring, or a substituted naphthalene ring substituted by 1 to 3 groups independently selected from $R^3$, $R^4$ and $R^5$, a benzene ring substituted with a $(C_1-C_5)$ alkylenedioxy group, or a substituted benzene ring substituted with a $(C_1-C_5)$ alkylenedioxy group further substituted by 1 to 3 groups independently selected from $R^3$, $R^4$ and $R^5$;

ring B' is an unsubstituted benzene ring, or a substituted benzene ring substituted by 1 to 3 groups independently selected from $R^3$, $R^4$ and $R^5$, an unsubstituted naphthalene ring, or a substituted naphthalene ring substituted by 1 to 3 groups independently selected from $R^3$, $R^4$ and $R^5$, a benzene ring substituted with a $(C_1-C_5)$-alkylenedioxy group, or a substituted benzene ring substituted with a $(C_1-C_5)$-alkylenedioxy group further substituted by 1 to 3 groups independently selected from $R^3$, $R^4$ and $R^5$;

$R^1$, $R^2$, $R^{1'}$ and $R^{2'}$ are independently selected from the group consisting of hydrogen, halogen, hydroxy, mercapto, $(C_1-C_5)$-alkyl, $(C_1-C_5)$-halogenalkyl, $(C_1-C_5)$-alkoxy, $(C_1-C_5)$ halogenalkoxy, $(C_3-C_5)$-alkenyloxy, $(C_4-C_7)$-cycloalkyloxy, $(C_3-C_7)$-cyloalkyl $(C_1-C_5)$ alkyloxy, aryl $(C_1-C_5)$ alkyloxy, $(C_1-C_5)$ alkylthio, $(C_1-C_5)$-alkylsulfinyl, $(C_1-C_5)$-alkylsulfonyl, amino, mono-$(C_1-C_5)$-alkylamino and di-$(C_1-C_5)$-alkylamino;

$R^3$, $R^4$, $R^5$, $R^{3'}$, $R^{4'}$ and $R^{5'}$ are independently selected from the group consisting of hydrogen, halogen, hydroxy, mercapto, $(C_1-C_5)$-alkyl, $(C_3-C_7)$-cycloalkyl, $(C_1-C_5)$-halogenalkyl, $(C_1-C_5)$-alkoxy, $(C_1-C_5)$ halogenalkoxy, $(C_3-C_5)$-alkenyloxy, $(C_4-C_7)$-cycloalkyloxy, $(C_3-C_7)$-cyloalkyl $(C_1-C_5)$ alkyloxy, aryl $(C_1-C_5)$ alkyloxy, $(C_1-C_5)$ alkylthio, $(C_1-C_5)$-alkylsulfinyl, $(C_1-C_5)$-alkylsulfonyl, amino, mono-$(C_1-C_5)$-alkylamino and di-$(C_1-C_5)$-alkylamino;

X is =O or =N—O—$R^7$, wherein $R^7$ is a hydrogen, $(C_1-C_5)$-alkyl, $(C_3-C_5)$-alkenyl, $(C_4-C_7)$-cycloalkyl, $(C_3-C_7)$-cycloalkyl$(C_1-C_5)$-alkyl, aryl, or aryl $(C_1-C_5)$-alkyl;

X' is =O or =N—O—$R^7$, wherein $R^7$ is a hydrogen, $(C_1-C_5)$-alkyl, $(C_3-C_5)$-alkenyl, $(C_4-C_7)$-cycloalkyl, $(C_3-C_7)$-cycloalkyl$(C_1-C_5)$-alkyl, aryl, or aryl $(C_1-C_5)$-alkyl;

$R^6$ is hydrogen, unsubstituted $(C_1-C_5)$-alkyl or substituted $(C_1-C_5)$-alkyl substituted by 1 to 3 groups independently selected from hydroxy, amino or halogen;

$R^{6'}$ is hydrogen, unsubstituted $(C_1-C_5)$-alkyl or substituted $(C_1-C_5)$ alkyl substituted by 1 to 3 groups independently selected from hydroxy, amino or halogen;

Y is -[J-N($R^8$)]p-[K-N($R^9$)]q-L- or -J-M-L-, wherein J, K and L are the same or different unsubstituted $(C_2-C_5)$-alkylenes or substituted $(C_2-C_5)$-alkylenes substituted with 1 or 2 $(C_1-C_5)$-alkyl;

M is an aliphatic ring having 2 nitrogen atoms; p and q are the same or different integers of 0 to 2; and $R^8$ and $R^9$ are independently hydrogen or $(C_1-C_5)$-alkyl, or a pharmaceutically acceptable salt thereof.

2. A compound of the formula [I] according to claim 1, wherein ring A is an unsubstituted nitrogen-containing 5 or 6 membered heteroaromatic ring or a substituted, nitrogen-containing 5 or 6 membered heteroaromatic ring substituted by one or two groups independently selected from $R^1$ and $R^2$;

ring A' is an unsubstituted nitrogen-containing 5 or 6 membered heteroaromatic ring or a substituted nitrogen-containing 5 or 6 membered heteroaromatic ring substituted by one or two groups independently selected from $R^{1'}$ and $R^{2'}$;

ring B is a benzene ring, naphthalene ring or benzene ring substituted with a $(C_1-C_5)$-alkylenedioxy group, or a substituted benzene ring, substituted naphthalene ring or substituted benzene ring substituted with a $(C_1-C_5)$-alkylenedioxy group further substituted by 1 to 3 groups independently selected from $R^3$, $R^4$ and $R^5$;

ring B' is a benzene ring, naphthalene ring or benzene ring substituted with a (C1–C5) alkylenedioxy group, or a substituted benzene ring, substituted naphthalene ring or substituted benzene ring substituted with a $(C_1-C_5)$-alkylenedioxy group further substituted by 1 to 3 groups independently selected from $R^{3'}$, $R^{4'}$ and $R^{5'}$;

$R^1$, $R^2$, $R^3$, $R^4$, $R^5$, $R^{1'}$, $R^{2'}$, $R^{3'}$, $R^{4'}$ and $R^{5'}$ are independently selected from the group consisting of hydrogen, halogen, hydroxy, mercapto, $(C_1-C_5)$-alkyl, $(C_1-C_5)$-halogenalkyl, $(C_1-C_5)$-alkoxy, $(C_1-C_5)$-halogenalkoxy, $(C_3-C_5)$-alkenyloxy, $(C_4-C_7)$-cycloalkyloxy, $(C_3-C_7)$-cyloalkyl$(C_1-C_5)$-alkyloxy, aryl$(C_1-C_5)$-alkyloxy, $(C_1-C_5)$-alkylthio, $(C_1-C_5)$-alkylsulfinyl, $(C_1-C_5)$-alkylsulfonyl, amino, mono-$(C_1-C_5)$-alkylamino or di-$(C_1-C_5)$-alkylamino;

X is $=$O or $=$N—O—$R^7$, wherein $R^7$ is a hydrogen, $(C_1-C_5)$-alkyl, $(C_3-C_5)$-alkenyl, $(C_4-C_7)$-cycloalkyl, $(C_3-C_7)$-cycloalkyl$(C_1-C_5)$-alkyl, aryl, or aryl $(C_1-C_5)$-alkyl;

X' is $=$O or $=$N—O—$R^7$, wherein $R^7$ is a hydrogen, $(C_1-C_5)$-alkyl, $(C_3-C_5)$-alkenyl, $(C_4-C_7)$-cycloalkyl, (C3–C7) cycloalkyl$(C_1-C_5)$-alkyl, aryl, or aryl $(C_1-C_5)$-alkyl;

$R^6$ is hydrogen, unsubstituted $(C_1-C_5)$-alkyl or substituted $(C_1-C_5)$-alkyl substituted by 1 to 3 groups independently selected from hydroxy, amino or halogen;

$R^{6'}$ is hydrogen, unsubstituted $(C_1-C_5)$-alkyl or substituted $(C_1-C_5)$-alkyl substituted by 1 to 3 groups independently selected from hydroxy, amino or halogen;

Y is -[J-N($R^8$)]p-[K-N($R^9$)]q-L- or -J-M-L-, wherein J, K and L are the same or different unsubstituted $(C_2-C_5)$ alkylenes or substituted $(C_2-C_5)$ alkylenes substituted with 1 or 2 $(C_1-C_5)$-alkyl;

M is an aliphatic ring having 2 nitrogen atoms; p and q are the same or different integers of 0 to 2; and $R^8$ and $R^9$ are independently hydrogen or $(C_1-C_5)$-alkyl, or a pharmaceutically acceptable salt thereof.

3. The compound of formula [I] according to claim 1, wherein ring A and ring A' are independently selected from the group consisting of pyridine, pyrazine, pyridazine, pyrimidine, oxazole, thiazole, isoxazole, isothiazole, imidazole, pyrrole, and triazole.

4. The compound of formula [I] according to claims 3 wherein ring A and ring A' are substituted with $R^1$ and $R^2$, and $R^{1'}$ and $R^{2'}$, respectively.

5. The compound of formula [I] according to claim 1, wherein the nitrogen-containing 5 or 6 membered heteroaromatic rings A and A' are pyridine.

6. The compound of formula [I] according to claim 5, wherein the nitrogen-containing 5 or 6 membered heterocyclic rings A and A' are substituted with $R^1$ and $R^2$, and $R^{1'}$ and $R^{2'}$, respectively.

7. The compound of formula [I] according to claim 1, wherein ring B and ring B' are benzene rings.

8. The compound of formula [I] according to claim 7, wherein the benzene rings are independently substituted by $R^3$, $R^4$ and $R^5$, or $R^{3'}$, $R^{4'}$ and $R^{5'}$ respectively.

9. The compound of formula [I] according to claim 1, wherein one of $R^1$ and $R^2$ is hydrogen and the other one is —$CH_3$.

10. The compound of formula [I] according to claim 1, wherein, $R^1$ and $R^2$ are both hydrogen.

11. The compound of formula [I] according to claim 1, wherein one of $R^{1'}$ and $R^{2'}$ is hydrogen and the other one is —$CH_3$.

12. The compound of formula [I] according to claim 1, wherein $R^{1'}$ and $R^{2'}$ are both hydrogen.

13. The compound of formula [I] according to claim 1, wherein $R^1$, $R^2$, $R^{1'}$ and $R^{2'}$ are all hydrogen.

14. The compound of formula [I] according to claim 1, wherein X and X' are $=$O.

15. The compound of formula [I] according to claim 1, wherein X and X' are $=$N—$OCH_3$.

16. The compound of formula [I] according to claim 1, wherein $R^3$, $R^4$, $R^5$, $R^{3'}$, $R^{4'}$ and $R^{5'}$ are independently selected from the group consisting of hydrogen, halogen, hydroxy, $(C_1-C_5)$-alkyl and $(C_1-C_5)$-alkoxy.

17. The compound of formula [I] according to claim 1, wherein $R^3$, $R^4$ and $R^5$ are:
a) all hydrogen, or
b) one is halogen and the two others are hydrogen, or
c) one is —$OCH_3$ and the two others are hydrogen, or
d) one is —OH and the two others are hydrogen.

18. The compound of formula [I] according to claim 17, wherein one of $R^3$, $R^4$ and $R^5$ is chloro and the two others are hydrogen.

19. The compound of formula [I] according to claim 1, wherein $R^{3'}$, $R^{4'}$ and $R^{5'}$ are:
a) all hydrogen, or
b) one is halogen and the two others are hydrogen, or
c) one is —$OCH_3$ and the two others are hydrogen, or
d) one is —OH and the two others are hydrogen.

20. The compound of formula [I] according to claim 19, wherein one of $R^{3'}$, $R^{4'}$ and R' is chloro and the two others are hydrogen.

21. The compound of formula [I] according to claim 1, wherein $R^3$, $R^4$, $R^5$, $R^{3'}$, $R^{4'}$ and $R^{5'}$ are all hydrogen.

22. The compound of formula [I] according to claim 1, wherein —N($R^6$)—Y—N($R^{6'}$)— is selected from the group consisting of —NH—$CH_2CH_2$—N($CH_3$)—$CH_2CH_2$—NH—,
—NH—$CH_2CH_2CH_2$—N($CH_3$)—$CH_2CH_2CH_2$—NH—,
—NH—$CH_2CH_2$—N($CH_3$)—$CH_2CH_2$—N($CH_3$)—$CH_2CH_2$—NH—,
—NH—$CH_2CH_2$—N($CH_3$)—$CH_2CH_2CH_2$—N($CH_3$)—$CH_2CH_2$—NH—,

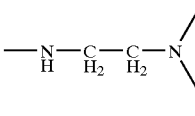
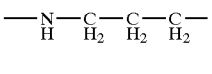

23. The compound of formula [I] according to claim 1, wherein —N($R^6$)—Y—N($R^{6'}$)— is —NH—$CH_2CH_2$—N($CH_3$)—$CH_2CH_2CH_2$—N($CH_3$)—$CH_2CH_2$—NH—.

24. The compound of formula [I] according to claim 1, wherein the compound is a) 3-methoxy-6-(2-{methyl-[2-(3-methoxy-7-oxo-7H-5,9-diaza-benzo[c]fluoren-6-ylamino)-ethyl]-amino}-ethylamino)-5,9-diaza-benzo[c]fluoren-7-one, b) 3-methoxy-6-{2-[(2-{[2-(3-methoxy-7-oxo-7H-5,9-diaza-benzo[c]fluoren-6-ylamino)-ethyl]-methyl-amino}-ethyl)-methyl-amino]-ethylamino}-5,9-diaza-benzo[c]fluoren-7-one, c) 3-methoxy-6-{2-[(3-{[2-(3-methoxy-7-oxo-7H-5,9-diaza-benzo[c]fluoren-6-ylamino)-ethyl]-methyl-amino}-propyl)-methyl-amino]-ethylamino}-5,9-diaza-benzo[c]fluoren-7-one, d) 6-(3-{methyl-[3-(7-oxo-7H-5,9-diaza-benzo[c]fluoren-6-ylamino)-propyl]-amino}-propylamino)-5,9-diaza-benzo[c]fluoren-7-one, e) 6-{2-[methyl-(3-{methyl-[2-(7-oxo-7H-5,9-diaza-benzo[c]fluoren-6-ylamino)-ethyl]-amino}-propyl)-amino]-ethylamino}-5,9-diaza-benzo[c]fluoren-7-one, f) 3-chloro-6-{2-[(3-{[2-(3-chloro-7-oxo-7H-5,9-diaza-benzo[c]fluoren-6-ylamino)-ethyl]-methyl-amino}-propyl)-methyl-amino]-ethylamino}-5,9-diaza-benzo[c]fluoren-7-one, g) 6-(2-{4-[2-(7-oxo-7H-5,9-diaza-benzo[c]fluoren-6-ylamino)-ethyl]-piperazin-1-yl}-ethylamino)-5,9-diaza-benzo[c]fluoren-7-one, h) 6-(3-{4-[3-(7-oxo-7H-5,9-diaza-benzo[c]fluoren-6-ylamino)-propyl]-piperazin-1-yl}-propylamino)-5,9-diaza-benzo[c]fluoren-7-one, i) 3-methoxy-6-{2-[(3-{[2-(3-methoxy-8-methyl-7-oxo-7H-5,9-diaza-benzo[c]fluoren-6-ylamino)-ethyl]-methyl-amino}-propyl)-methyl-amino]-ethylamino}-8-methyl-5,9-diaza-benzo[c]fluoren-7-one, j) 6-{2-[methyl-(3-{methyl-[2-(7-oxo-7H-5,10-diaza-benzo[c]fluoren-6-ylamino)-ethyl]-amino}-propyl)-amino]-ethylamino}-5,10-diaza-benzo[c]fluoren-7-one, k) 3-methoxy-6-{2-[(3-{[2-(3-methoxy-4-methyl-7-oxo-7H-5,10-diaza-benzo[c]fluoren-6-ylamino)-ethyl]-methyl-amino}-propyl)-methyl-amino]-ethylamino}-4-methyl-5,10-diaza-benzo[c]fluoren-7-one, l) 3-chloro-6-{2-[(3-{[2-(3-chloro-7-oxo-7H-5,10-diaza-benzo[c]fluoren-6-ylamino)-ethyl]-methyl-amino}-propyl)-methyl-amino]-ethylamino}-5,10-diaza-benzo[c]fluoren-7-one, m) 11-chloro-6-{2-[(3-{[2-(11-chloro-3-methoxy-4-methyl-7-oxo-7H-5,10-diaza-benzo[c]fluoren-6-ylamino)-ethyl]-methyl-amino}-propyl)-methyl-amino]-ethylamino}-3-methoxy-4-methyl-5,10-diaza-benzo[c]fluoren-7-one, n) 3-methoxy-6-{2-[(3-{[2-(3-methoxy-9-methyl-7-oxo-7H-5,10-diaza-benzo[c]fluoren-6-ylamino)-ethyl]-methyl-amino}-propyl)-methyl-amino]-ethylamino}-9-methyl-5,10-diaza-benzo[c]fluoren-7-one, o) 6-{2-[methyl-(3-{methyl-[2-(7-oxo-7H-5,10-diaza-benzo[c]fluoren-6-ylamino)-ethyl]-amino}-propyl)-amino]-ethylamino}-5,9-diaza-benzo[c]fluoren-7-one, p) 3-methoxy-6-{2-[methyl-(3-{methyl-[2-(7-oxo-7H-5,9-diaza-benzo[c]fluoren-6-ylamino)-ethyl]-amino}-propyl)-amino]-ethylamino}-5,9-diaza-benzo[c]fluoren-7-one, q) 3-hydroxy-6-{2-[(3-{[2-(3-hydroxy-7-oxo-7H-5,9-diaza-benzo[c]fluoren-6-ylamino)-ethyl]-methyl-amino}-propyl)-methyl-amino]-ethylamino}-5,9-diaza-benzo[c]fluoren-7-one, or r) 6-(3-{[3-(7-methoxyimino-7H-5,9-diaza-benzo[c]fluoren-6-ylamino)-propyl]-methyl-amino}-propylamino)-5,9-diaza-benzo[c]fluoren-7-one O-methyl-oxime.

25. The compound of formula [I] according to claim 1, wherein the compound is a) 3-methoxy-6-{2-[(3-{[2-(3-methoxy-7-oxo-7H-5,9-diaza-benzo[c]fluoren-6-ylamino)-ethyl]-methyl-amino}-propyl)-methyl-amino]-ethylamino}-5,9-diaza-benzo[c]fluoren-7-one, b) 6-{2-[methyl-(3-{methyl-[2-(7-oxo-7H-5,9-diaza-benzo[c]fluoren-6-ylamino)-ethyl]-amino}-propyl)-amino]-ethylamino}-5,9-diaza-benzo[c]fluoren-7-one, c) 3-chloro-6-{2-[(3-{[2-(3-chloro-7-oxo-7H-5,9-diaza-benzo[c]fluoren-6-ylamino)-ethyl]-methyl-amino}-propyl)-methyl-amino]-ethylamino}-5,9-diaza-benzo[c]fluoren-7-one, d) 6-(3-{4-[3-(7-oxo-7H-5,9-diaza-benzo[c]fluoren-6-ylamino)-propyl]-piperazin-1-yl}-propylamino)-5,9-diaza-benzo[c]fluoren-7-one, e) 6-{2-[methyl-(3-{methyl-[2-(7-oxo-7H-5,10-diaza-benzo[c]fluoren-6-ylamino)-ethyl]-amino}-propyl)-amino]-ethylamino}-5,10-diaza-benzo[c]fluoren-7-one, f) 3-chloro-6-{2-[(3-{[2-(3-chloro-7-oxo-7H-5,10-diaza-benzo[c]fluoren-6-ylamino)-ethyl]-methyl-amino}-propyl)-methyl-amino]-ethylamino}-5,10-diaza-benzo[c]fluoren-7-one, g) 3-methoxy-6-{2-[(3-{[2-(3-methoxy-9-methyl-7-oxo-7H-5,10-diaza-benzo[c]fluoren-6-ylamino)-ethyl]-methyl-amino}-propyl)-methyl-amino]-ethylamino}-9-methyl-5,10-diaza-benzo[c]fluoren-7-one, h) 6-{2-[methyl-(3-{methyl-[2-(7-oxo-7H-5,10-diaza-benzo[c]fluoren-6-ylamino)-ethyl]-amino}-propyl)-amino]-ethylamino}-5,9-diaza-benzo[c]fluoren-7-one, or i) 3-methoxy-6-{2-[methyl-(3-{methyl-[2-(7-oxo-7H-5,9-diaza-benzo[c]fluoren-6-ylamino)-ethyl]-amino}-propyl)-amino]-ethylamino}-5,9-diaza-benzo[c]fluoren-7-one.

26. A pharmaceutical composition comprising a compound of formula [I] according to claim 1 as an active ingredient and a pharmaceutically acceptable carrier.

27. A method for treating a cell proliferative disorder selected from the group consisting of colorectal cancer, lung cancer, breast cancer, stomach cancer, cervical cancer and bladder cancer, comprising administering to a patient in need thereof a therapeutically effective amount of a compound of formula [I],

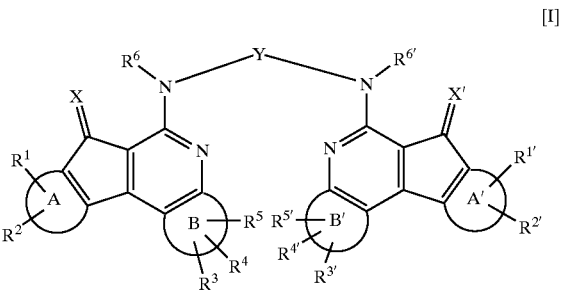

wherein ring A is an unsubstituted nitrogen-containing 5 or 6 membered heteroaromatic ring or a substituted nitrogen-containing 5 or 6 membered heteroaromatic ring substituted by one or two groups independently selected from R¹ and R²;

ring A' is an unsubstituted nitrogen-containing 5 or 6 membered heteroaromatic ring or a substituted nitrogen-containing 5 or 6 membered heteroaromatic ring substituted by one or two groups independently selected from R¹' and R²';

ring B is an unsubstituted benzene ring, or a substituted benzene ring substituted by 1 to 3 groups independently selected from R³, R⁴ and R⁵, an unsubstituted naphthalene ring, or a substituted naphthalene ring substituted by 1 to 3 groups independently selected from R³, R⁴ and R⁵, a benzene ring substituted with a ($C_1$–$C_5$) alkylenedioxy group, or a substituted benzene ring substituted with a ($C_1$–$C_5$) alkylenedioxy group further substituted by 1 to 3 groups independently selected from R³, R⁴ and R⁵;

ring B' is an unsubstituted benzene ring, or a substituted benzene ring substituted by 1 to 3 groups independently selected from R³, R⁴ and R⁵, an unsubstituted naphthalene ring, or a substituted naphthalene ring substituted by 1 to 3 groups independently selected from R³, R⁴ and R⁵, a benzene ring substituted with a ($C_1$–$C_5$)-alkylenedioxy group, or a substituted benzene ring substituted with a ($C_1$–$C_5$)-alkylenedioxy group further substituted by 1 to 3 groups independently selected from R³, R⁴ and R⁵;

R¹, R², R¹' and R²' are independently selected from the group consisting of hydrogen, halogen, hydroxy, mercapto, ($C_1$–$C_5$)-alkyl, ($C_1$–$C_5$)-halogenalkyl, ($C_1$–$C_5$)-alkoxy, ($C_1$–$C_5$) halogenalkoxy, ($C_3$–$C_5$)-alkenyloxy, ($C_4$–$C_7$)-cycloalkyloxy, ($C_3$–$C_7$)-cyloalkyl ($C_1$–$C_5$) alkyloxy, aryl ($C_1$–$C_5$) alkyloxy, ($C_1$–$C_5$) alkylthio, ($C_1$–$C_5$)-alkylsulfinyl, ($C_1$–$C_5$)-alkylsulfonyl, amino, mono-($C_1$–$C_5$)-alkylamino and di-($C_1$–$C_5$)-alkylamino;

R³, R⁴, R⁵, R³', R⁴' and R⁵ are independently selected from the group consisting of hydrogen, halogen, hydroxy, mercapto, ($C_1$–$C_5$)-alkyl, ($C_3$–$C_7$)-cycloalkyl, ($C_1$–$C_5$)-halogenalkyl, ($C_1$–$C_5$)-alkoxy, ($C_1$–$C_5$) halogenalkoxy, ($C_3$–$C_5$)-alkenyloxy, ($C_4$–$C_7$) cycloalkyloxy, ($C_3$–$C_7$)-cyloalkyl ($C_1$–$C_5$) alkyloxy, aryl ($C_1$–$C_5$) alkyloxy, ($C_1$–$C_5$) alkylthio, ($C_1$–$C_5$)-alkylsulfinyl, ($C_1$–$C_5$)-alkylsulfonyl, amino, mono-($C_1$–$C_5$)-alkylamino and di-($C_1$–$C_5$)-alkylamino;

X is =O or =N—O—R⁷, wherein R⁷ is a hydrogen, ($C_1$–$C_5$)-alkyl, ($C_3$–$C_5$)-alkenyl, ($C_4$–$C_7$)-cycloalkyl, ($C_3$–$C_7$)-cycloalkyl($C_1$–$C_5$)-alkyl, aryl, or aryl ($C_1$–$C_5$)-alkyl;

X' is =O or =N—O—R⁷, wherein R⁷ is a hydrogen, ($C_1$–$C_5$)-alkyl, ($C_3$–$C_5$)-alkenyl, ($C_4$–$C_7$)-cycloalkyl, ($C_3$–$C_7$)-cycloalkyl($C_1$–$C_5$)-alkyl, aryl, or aryl ($C_1$–$C_5$)-alkyl;

R⁶ is hydrogen, unsubstituted ($C_1$–$C_5$)-alkyl or substituted ($C_1$–$C_5$)-alkyl substituted by 1 to 3 groups independently selected from hydroxy, amino or halogen;

R⁶' is hydrogen, unsubstituted ($C_1$–$C_5$)-alkyl or substituted ($C_1$–$C_5$) alkyl substituted by 1 to 3 groups independently selected from hydroxy, amino or halogen;

Y is -[J-N(R⁸)]p-[K-N(R⁹)]q-L- or -J-M-L-, wherein J, K and L are the same or different unsubstituted ($C_2$–$C_5$)-alkylenes or substituted ($C_2$–$C_5$)-alkylenes substituted with 1 or 2 ($C_1$–$C_5$)-alkyl;

M is an aliphatic ring having 2 nitrogen atoms; p and q are the same or different integers of 0 to 2; and R⁸ and R⁹ are independently hydrogen or ($C_1$–$C_5$)-alkyl, or a pharmaceutically acceptable salt thereof.

28. A process for producing polycyclic compounds of the formula [I],

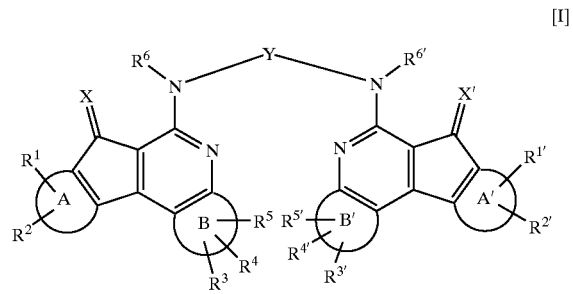

wherein ring A is an unsubstituted nitrogen-containing 5 or 6 membered heteroaromatic ring or a substituted nitrogen-containing 5 or 6 membered heteroaromatic ring substituted by one or two groups independently selected from R¹ and R²;

ring A' is an unsubstituted nitrogen-containing 5 or 6 membered heteroaromatic ring or a substituted nitrogen-containing 5 or 6 membered heteroaromatic ring substituted by one or two groups independently selected from R¹' and R²';

ring B is an unsubstituted benzene ring, or a substituted benzene ring substituted by 1 to 3 groups independently selected from R³, R⁴ and R⁵, an unsubstituted naphthalene ring, or a substituted naphthalene ring substituted by 1 to 3 groups independently selected from R³, R⁴ and R⁵, a benzene ring substituted with a ($C_1$–$C_5$) alkylenedioxy group, or a substituted benzene ring substituted with a ($C_1$–$C_5$) alkylenedioxy group further substituted by 1 to 3 groups independently selected from R³, R⁴ and R⁵;

ring B' is an unsubstituted benzene ring, or a substituted benzene ring substituted by 1 to 3 groups independently selected from R³, R⁴ and R⁵, an unsubstituted naphthalene ring, or a substituted naphthalene ring substituted by 1 to 3 groups independently selected from R³, R⁴ and R⁵, a benzene ring substituted with a ($C_1$–$C_5$)-alkylenedioxy group, or a substituted benzene ring substituted with a ($C_1$–$C_5$)-alkylenedioxy group further substituted by 1 to 3 groups independently selected from R³, R⁴ and R⁵;

R¹, R², R¹' and R²' are independently selected from the group consisting of hydrogen, halogen, hydroxy, mercapto, ($C_1$–$C_5$)-alkyl, ($C_1$–$C_5$)-halogenalkyl, ($C_1$–$C_5$)-alkoxy, ($C_1$–$C_5$) halogenalkoxy, ($C_3$–$C_5$)-alkenyloxy, ($C_4$–$C_7$)-cycloalkyloxy, ($C_3$–$C_7$)-cyloalkyl ($C_1$–$C_5$) alkyloxy, aryl ($C_1$–$C_5$) alkyloxy, ($C_1$–$C_5$) alkylthio, ($C_1$–$C_5$)-alkylsulfinyl, ($C_1$–$C_5$)-alkylsulfonyl, amino, mono-($C_1$–$C_5$)-alkylamino and di-($C_1$–$C_5$)-alkylamino;

R³, R⁴, R⁵, R³', R⁴' and R⁵ are independently selected from the group consisting of hydrogen, halogen, hydroxy, mercapto, ($C_1$–$C_5$)-alkyl, ($C_3$–$C_7$)-cycloalkyl, ($C_1$–$C_5$)-halogenalkyl, ($C_1$–$C_5$)-alkoxy, ($C_1$–$C_5$) halogenalkoxy, ($C_3$–$C_5$)-alkenyloxy, ($C_4$–$C_7$)-cycloalkyloxy, ($C_3$–$C_7$)-cyloalkyl ($C_1$–$C_5$) alkyloxy, aryl ($C_1$–$C_5$) alkyloxy, ($C_1$–$C_5$) alkylthio, ($C_1$–$C_5$)-alkylsulfinyl, ($C_1$–$C_5$)-alkylsulfonyl, amino, mono-($C_1$–$C_5$)-alkylamino and di-($C_1$–$C_5$)-alkylamino;

R⁶ is hydrogen, unsubstituted ($C_1$–$C_5$)-alkyl or substituted ($C_1$–$C_5$)-alkyl substituted by 1 to 3 groups independently selected from hydroxy, amino or halogen;

$R^{6'}$ is hydrogen, unsubstituted $(C_1-C_5)$-alkyl or substituted $(C_1-C_5)$ alkyl substituted by 1 to 3 groups independently selected from hydroxy, amino or halogen;

Y is -[J-N($R^8$)]p-[K-N($R^9$)]q-L- or -J-M-L-, wherein J, K and L are the same or different unsubstituted $(C_2-C_5)$-alkylenes or substituted $(C_2-C_5)$-alkylenes substituted with 1 or 2 $(C_1-C_5)$-alkyl;

M is an aliphatic ring having 2 nitrogen atoms; p and q are the same or different integers of 0 to 2; and $R^8$ and $R^9$ are independently hydrogen or $(C_1-C_5)$-alkyl, and X and X' are O, which comprises reacting either two compounds of the formulae [VI], [VI'], [VII] or [VII'],

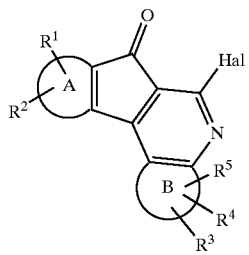

[VI]

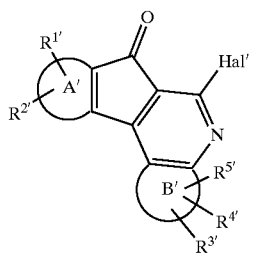

[VI']

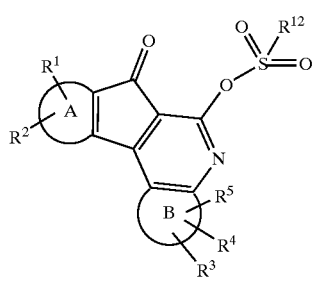

[VII]

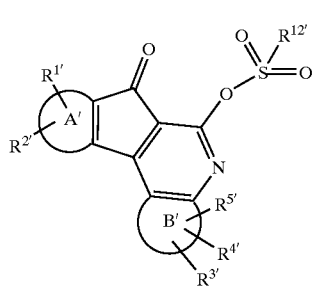

[VII']

wherein ring A, ring B, $R^1$, $R^2$, $R^3$, $R^4$, $R^5$, ring A', ring B', $R^{1'}$, $R^{2'}$, $R^{3'}$, $R^{4'}$ and $R^{5'}$ are the same as defined above; Hal and Hal' are the same or different halogen atoms; and $R^{12}$ and $R^{12'}$ are independently $(C_1-C_5)$-alkyl, $(C_1-C_5)$-halogenalkyl or aryl, with a compound of the formula [VIII],

[VIII]

wherein $R^6$, Y and $R^{6'}$ are the same as defined above.

* * * * *

UNITED STATES PATENT AND TRADEMARK OFFICE
CERTIFICATE OF CORRECTION

PATENT NO. : 6,946,472 B2
DATED : September 20, 2005
INVENTOR(S) : Kenichi Kawasaki et al.

It is certified that error appears in the above-identified patent and that said Letters Patent is hereby corrected as shown below:

<u>Title page,</u>
Item [73], Assignee, should read -- Hoffmann-La Roche Inc., Nutley, NJ (US) --.

<u>Column 47,</u>
Line 34, "=N-O-7, wherein 7 is hydrogen" should be -- =N-O-7', wherein 7' is hydrogen, --.

Signed and Sealed this

Twenty-fifth Day of April, 2006

JON W. DUDAS
*Director of the United States Patent and Trademark Office*